United States Patent
Likhacheva

(10) Patent No.: US 12,005,219 B2
(45) Date of Patent: Jun. 11, 2024

(54) SYSTEMS AND METHODS FOR CONFORMING TREATMENT APPLICATORS TO NON-UNIFORM SURFACES

(71) Applicant: Anna O. Likhacheva, El Macero, CA (US)

(72) Inventor: Anna O. Likhacheva, El Macero, CA (US)

(*) Notice: Subject to any disclaimer, the term of this patent is extended or adjusted under 35 U.S.C. 154(b) by 878 days.

(21) Appl. No.: 17/099,443

(22) Filed: Nov. 16, 2020

(65) Prior Publication Data

US 2021/0146106 A1  May 20, 2021

Related U.S. Application Data

(60) Provisional application No. 62/937,216, filed on Nov. 18, 2019.

(51) Int. Cl.
*A61M 37/00* (2006.01)
*A61B 18/14* (2006.01)
(Continued)

(52) U.S. Cl.
CPC ..... *A61M 37/0015* (2013.01); *A61B 18/1477* (2013.01); *A61N 5/1027* (2013.01);
(Continued)

(58) Field of Classification Search
CPC ...... A61M 37/0015; A61M 2037/0023; A61M 2037/003; A61M 2037/0061;
(Continued)

(56) References Cited

U.S. PATENT DOCUMENTS

| 4,947,842 A | 8/1990 | Marchosky et al. |
| 5,800,394 A | 9/1998 | Yoon et al. |

(Continued)

FOREIGN PATENT DOCUMENTS

EP  0719571 A2  7/1996

OTHER PUBLICATIONS

International Search Report & Written Opinion dated Feb. 11, 2021 in Int'l PCT Patent Appl. Serial No. PCT/US2020/060768 (0210).
(Continued)

*Primary Examiner* — Amber R Stiles
(74) *Attorney, Agent, or Firm* — Resonance IP Law, PC

(57) ABSTRACT

Systems and methods are provided for delivering therapy using an applicator guide and a plurality of catheters for delivering, e.g., radiation, drug, RF, laser or ultrasound therapy. The applicator guide includes a through hole channels through which the catheters may be introduced. The through hole channels may be sized such that the plurality of catheters may freely and independently traverse the through hole channels. By positioning the applicator guide over a target area of a patient's skin, the catheters are free to make contact with the patient's skin and conform to any contours of the patient's skin. The catheters may be microneedles that may be locked in the conformed orientation, such that the microneedles may non-invasively penetrate the patient's skin to deliver the therapy transdermally. The applicator guide may be coupled to an afterloader, drug reservoir, pulse generator, and/or power generator controlled by a healthcare provider via a computing device.

20 Claims, 16 Drawing Sheets

(51) Int. Cl.
*A61N 5/10* (2006.01)
*A61N 7/02* (2006.01)
*A61B 18/00* (2006.01)
*A61B 18/20* (2006.01)
*A61N 7/00* (2006.01)

(52) U.S. Cl.
CPC ........ *A61N 7/02* (2013.01); *A61B 2018/0047* (2013.01); *A61B 2018/00577* (2013.01); *A61B 18/20* (2013.01); *A61B 2018/2005* (2013.01); *A61M 2037/0023* (2013.01); *A61M 2037/003* (2013.01); *A61M 2037/0061* (2013.01); *A61M 2205/36* (2013.01); *A61N 2007/003* (2013.01)

(58) Field of Classification Search
CPC ........... A61M 2205/36; A61B 18/1477; A61B 18/20; A61B 2018/0047; A61B 2018/00577; A61B 2018/2005; A61N 5/1027; A61N 7/02; A61N 2007/003; A61N 2005/1018; A61N 5/1001
See application file for complete search history.

(56) References Cited

U.S. PATENT DOCUMENTS

| | | | |
|---|---|---|---|
| 7,658,725 B2 | 2/2010 | Bialecki et al. | |
| 7,785,301 B2 | 8/2010 | Yuzhakov | |
| 8,414,548 B2 | 4/2013 | Yuzhakov | |
| 2004/0243200 A1 | 12/2004 | Turner et al. | |
| 2005/0251235 A1 | 11/2005 | Schlorff et al. | |
| 2007/0270627 A1 | 11/2007 | Cutrer et al. | |
| 2010/0228207 A1* | 9/2010 | Ballakur | A61B 17/3203 604/319 |
| 2016/0361194 A1 | 12/2016 | Hautvast et al. | |

OTHER PUBLICATIONS

International Search Report & Written Opinion dated Dec. 9, 2021 in Int'l PCT Patent Appl. Serial No. PCT/US2021/046141 (0310).
Pieters, et al., GEC-ESTRO/ACROP Recommendations For Performing Bladder-Sparing Treatment With Brachytherapy For Muscle-Invasive Bladder Carcinoma, Radiotherapy and Oncology, 122(3):340-346 (2017).
Rzhevskiy, et al., Microneedles as the technique of drug delivery enhancement in diverse organs and tissues, Journal of Controlled Release, 270:184-202 (2018).
Szunerits, et al., Heat: A Highly Efficient Skin Enhancer For Transdermal Drug Delivery, Frontiers in Bioengineering and Biotechnology, 6:1-13, Article 15 (2018).

* cited by examiner

SYSTEMS AND METHODS FOR CONFORMING TREATMENT APPLICATORS TO NON-UNIFORM SURFACES

CROSS-REFERENCE TO RELATED APPLICATION

This application claims priority to U.S. Provisional Application No. 62/937,216, filed on Nov. 18, 2019, the entire contents of which are hereby incorporated herein by reference

FIELD OF THE INVENTION

The disclosure relates to systems and methods for improving application of treatment applicators to surfaces of a patient that are non-uniform.

BACKGROUND OF THE INVENTION

Skin cancer is the most common type of cancer in the United States with an annual incidence rate over five million cases. Basal cell carcinoma (BCC) and cutaneous squamous cell carcinoma (cSCC) account for over 95% of all skin cancer diagnoses.

A variety of treatment options are currently available to treat skin cancer. Some of the most common treatment approaches include surgical excision, cryotherapy, radiotherapy, and topical agents. Surgical excision is considered the "gold standard" for curative treatment of BCC and cSCC. While excision may be the preferred approach, it is often painful and may result in disfigurement. Cryotherapy and topical agents are limited in their application and success rates.

Radiotherapy plays a critical role in skin cancer treatment in both definitive and adjuvant settings. Brachytherapy is one form of radiation delivery that may be used in skin cancer treatment. Brachytherapy generally involves placing radioactive material next to the treatment target via an applicator. Brachytherapy may involve an interstitial approach or may be used to treat the surface of a patient's skin without entering the patient's body.

Current skin surface brachytherapy treatment systems are performed using either pre-fabricated shielded fixed geometry applicators or custom applicators made with thermoplastic material. Current systems typically involve multi-channel catheters that run parallel to the surface of the skin. As the radioactive material must run through these channels to reach the target tissue, the channels are limited in their geometry. While channels may be formed to fit the contours of the patient's face, this process is expensive and time consuming.

In addition, other types of skin-based diseases may require drug delivery systems to effectively deliver drug therapy to the patient. For example, dermatological topical pharmaceutical formulations such as foams, creams, lotions, gels, etc., are generally used to target skin-based diseases. However, many drug molecules are too large or too lipophobic to penetrate the stratum corneum (SC) barrier, the outermost layer of the skin. The hydrophobic lipids of the SC may block the entry of most topically applied drugs. Thus, such drugs would need to be delivered beyond the epidermis into the dermis or deeper.

Transdermal delivery systems (TDDSs), which use the skin as the main route of drug delivery, have been shown to offer advantages over topical as well as intravenous drug delivery routes. In addition to being non-invasive and painless, TDDSs may advantageously deliver drugs effectively without requiring frequent administrations to maintain constant drug delivery.

U.S. Pat. Nos. 7,658,728, 7,785,301, 8,414,548 describe microneedle patches for transdermal drug delivery such as the AdminPatch® Microneedle Arrays (made available by nanoBioSciences, LLC, Sunnyvale, California). These patches are static devices used to create micropores in the outermost layer of the skin, and thus, do not conform to concave or convex features of the skin. Even application and delivery of these drugs may be vital to the effectiveness of the treatment and satisfactory outcome.

In view of the foregoing drawbacks of the previously known systems and methods for application of radiation therapy and other therapies (e.g., drug, ultrasound, RF, laser, etc.) to surfaces of a patient that are contoured and non-uniform, it would be desirable to provide systems and methods for precisely applying therapy to non-uniform skin of the patient. It further would be desirable to provide systems and methods for application of therapy to dynamic skin surfaces.

In addition, it would be desirable to provide systems and methods for transdermal application of therapy to dynamic skin surfaces.

SUMMARY OF THE INVENTION

The present invention is directed to a radiotherapy system having an applicator guide with a plurality of through hole channels in which a plurality of catheters may be disposed. The catheters may move freely and independently within the through hole channels and may conform to a patients skin when the applicator guide and catheters are positioned over a non-uniform portion of the patient's anatomy. The catheters may be connected via transfer tubes to an afterloader, which sends radioactive source through the catheters. A healthcare provider using a computing device may control the afterloader.

In accordance with the principles of the present disclosure, an exemplary radiotherapy system may include an applicator guide having a plurality of through hole channels extending from a first side of the guide structure to a second side of the guide structure. The plurality of through hole channels may be formed in an array. A plurality of catheters configured to deliver radiotherapy may be disposed in respective through hole channels in the applicator guide. The plurality of catheters may be independently and freely movable within the respective through hole channels and responsive to contact by distal tips of the plurality of catheters with an area of the patient's skin such that the distal tips independently move to conform to contours of the area of the patient's skin and to contact the area. The plurality of catheters may be configured to selectively deliver radiotherapy to a target area within the area of the patent's skin while the plurality of catheters are positioned in a conformed orientation.

An exemplary method for delivering radiotherapy to a patient in accordance with the principles of the present disclosure, may include positioning an applicator guide over a target area of the patient and conforming the plurality of catheters to the target area of the patient. The applicator guide may include a plurality of through hole channels each loaded with a catheter of a plurality of catheters. The plurality of catheters may be independently and freely movable within the respective through hole of the plurality of through holes and responsive to contact by distal tips of the plurality of catheters with the target area of the patient such that the distal tips independently move to conform to contours of the target area of the patient. The method may finally include delivering radioactive material to at least one of the plurality of catheters.

An exemplary system for delivering radiotherapy to a non-uniform portion of a patient's skin in accordance with the principles of the present disclosure, may include an applicator assembly, an afterloader connected to each one of the plurality of catheters via a plurality of transfer tubes, and a computing device in communication with the afterloader and configured to instruct the afterloader to deliver radioactive material to the plurality of catheters.

The applicator assembly may include an applicator guide configured to maintain a plurality of catheters in an upright position and a plurality of catheters configured to deliver radiotherapy. Each one of the plurality of catheters may be independently and freely movable with respect to the applicator guide and one another and responsive to contact by distal tips of the plurality of catheters with an area of the patient's skin such that the distal tips independently move to conform to contours of the area of the patient's skin and to contact the area. Further, the plurality of catheters may be configured to selectively deliver radiotherapy to a target area within the area of the skin while the plurality of catheters are positioned in a conformed orientation.

In accordance with another aspect of the present disclosure another exemplary therapy delivery system is provided. The system may include an applicator guide having a plurality of through hole channels extending from a first side of the applicator guide to a second side of the applicator guide, the plurality of through hole channels arranged in an array. The system further may include a plurality of catheters for delivering a therapy, each catheter of the plurality of catheters disposed in respective through hole channels of the plurality of through hole channels in the applicator guide. The plurality of catheters are independently and freely movable in at least one degree of freedom within the respective through hole channels such that the plurality of catheters may conform to contours of an area of the patient's skin and to contact the area in a conformed orientation. Accordingly, the plurality of catheters may deliver therapy to at least a portion of the area of the patent's skin while the plurality of catheters are positioned in the conformed orientation.

The plurality of catheters may include a plurality of microneedles sized and shaped to non-invasively penetrate a stratum corneum (SC) of the patient's skin, such that the plurality of microneedles may selectively deliver therapy to the at least a portion of the area transdermally. For example, the applicator guide may include a plurality of locks, each one of the plurality of locks operatively coupled to a respective one of the plurality of microneedles to lock the respective one of the plurality of microneedles in the conformed orientation. Thus, the plurality of microneedles may non-invasively penetrate the stratum corneum (SC) of the patient's skin in the conformed orientation. The plurality of locks may be activated individually or together.

In some embodiments, the plurality of microneedles may selectively deliver a drug to the at least a portion of the area transdermally. For example, the plurality of microneedles may be coated with the drug. Additionally or alternatively, the plurality of microneedles may include an internal lumen, such that the drug may be delivered to the at least a portion of the area transdermally through the internal lumen of the plurality of microneedles. Additionally or alternatively, the drug may be embedded within the plurality of microneedles, such that at least a portion of the plurality of microneedles may be dissolved to deliver the drug to the at least a portion of the area transdermally.

In some embodiments, the plurality of catheters may be operatively coupled to a pulse generator to selectively deliver RF energy to the at least a portion of the area. In some embodiments, the plurality of catheters are operatively coupled to an ultrasound transducer to selectively deliver ultrasound energy to the at least a portion of the area. In some embodiments, the plurality of catheters are operatively coupled to an afterloader to selectively deliver radiotherapy to the at least a portion of the area. For example, each of the plurality of catheters may be individually activated to deliver radiation. The afterloader may be connected to each one of the plurality of catheters via a plurality of transfer tubes. Accordingly, the system further may include a computing device in communication with the afterloader that may instruct the afterloader to deliver radioactive material to the plurality of catheters. Additionally, one or more of the plurality of catheters may apply heat while simultaneously delivering therapy to the target area.

In accordance with another aspect of the present disclosure another exemplary method for delivering therapy to a patient is provided. The method may include positioning the applicator guide over a target area of the patient; loading the plurality of catheters into through hole channels of the plurality of through hole channels such that each of the plurality of through hole channels is loaded with the catheter of the plurality of catheters; conforming the plurality of catheters to the target area of the patient in a conformed orientation; and delivering therapy to the target area of the patient via at least one of the plurality of catheters in the conformed orientation.

The method further may include the locking the microneedles in the conformed orientation. In addition, the method may include penetrating the stratum corneum (SC) of the patient's skin with the plurality of microneedles in the conformed orientation, such that delivering therapy to the target area of the patient includes delivering therapy to the target area of the patient transdermally.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE DISCLOSURE

The system of the present disclosure includes systems and methods for delivering and guiding applicators, e.g., radiotherapy applicators or microneedles, to non-uniform surfaces in a manner to permit catheters to conform to curved surfaces and even adapt to dynamic surfaces. The system involves an applicator guide and may further involve a plurality of catheters, transfer tubes, an afterloader for delivering radioactive material, a drug reservoir for delivering drug therapy, or an energy source for delivering energy, and a computing device.

To deliver radiotherapy to a skin target on a patient, the plurality of catheters may be positioned through the applicator guide and the computing device may control the afterloader to deliver the radioactive source through the transfer tubes to a pre-specified position within the catheter, such as the tip. The tip may be blunt and/or have a flat cap.

Figure 1A:
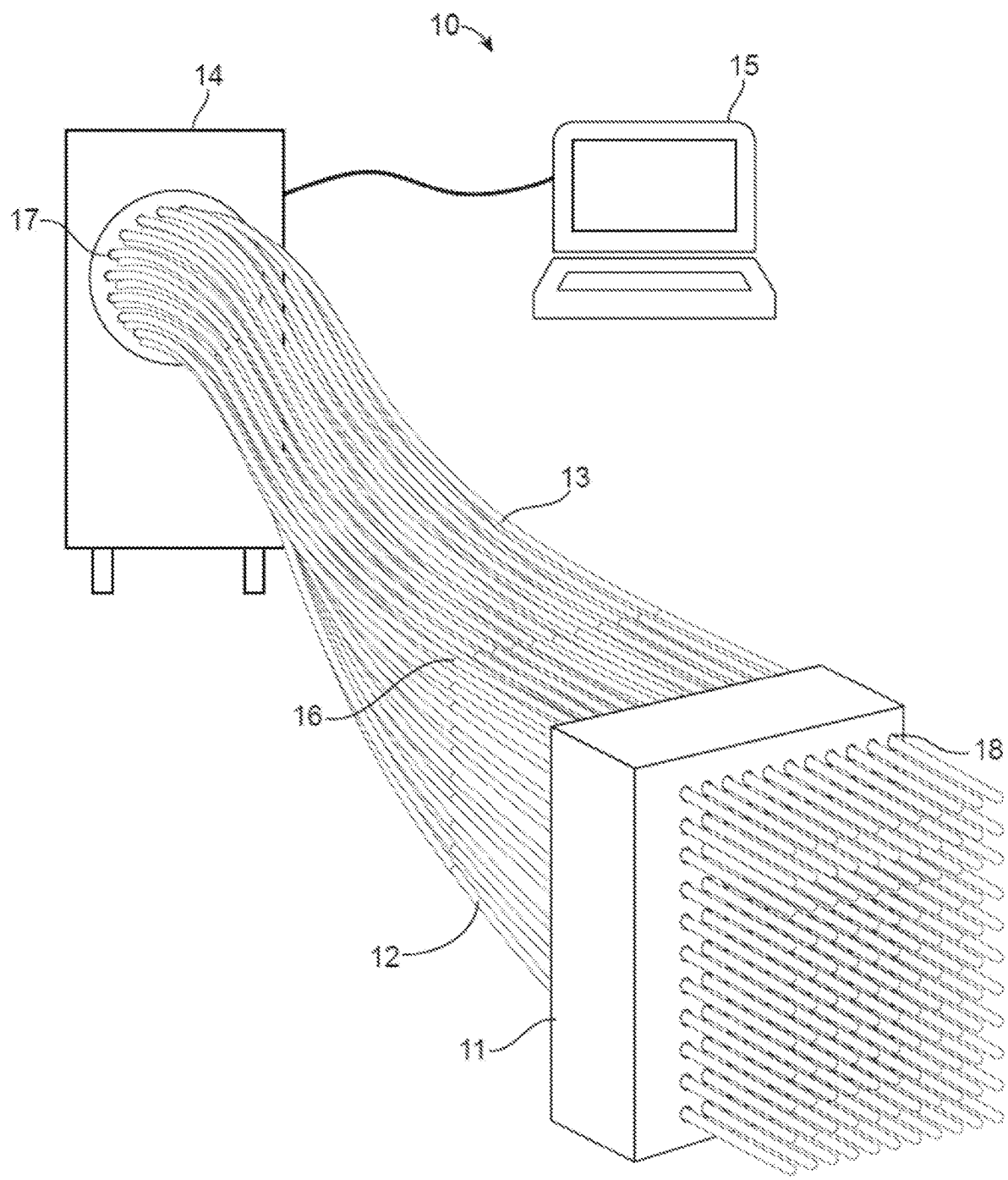
FIG. 1A illustrates the radiotherapy system including the afterloader, applicator guide, and computing device running afterloader software.

Referring to FIG. 1A, radiotherapy system 10 is illustrated. Radiotherapy system 10 may include applicator guide 11, catheters 12, transfer tubes 13, afterloader 14, and computing device 15. As is shown in FIG. 1A, catheters 12 may be positioned entirely through applicator guide 11 via through holes 18 and may be coupled to transfer tube 13 at connecting interface 16. Transfer tube 13 may also connect to afterloader 14 at connecting interface 16. Computing device 15 may be a standalone computing device, or may be incorporated into afterloader 14. Computing device 15 may communicate with afterloader 14 via any well-known wired or wireless connection (BlueTooth, Wi-Fi Direct, etc.).

Figure 1B:
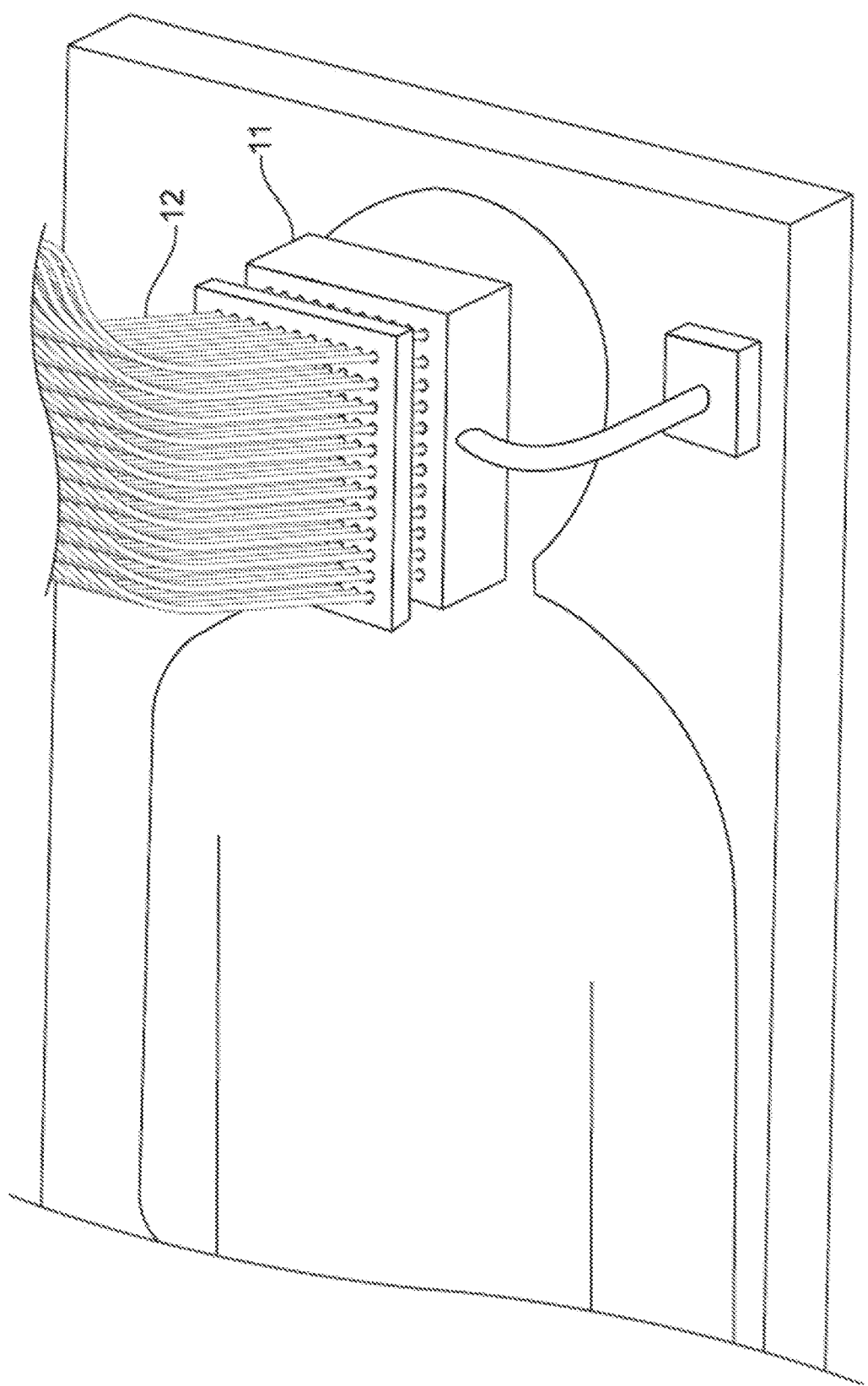
FIG. 1B illustrates an exemplary applicator guide positioned on the face of a patient.

Referring now to FIG. 1B, applicator guide 11 is illustrated being positioned over a patient to deliver radiotherapy via catheters 12. Catheters 12 will extend through applicator guide 11 and lie to rest on the surface of the patient. Catheters 12 are free to move within applicator guide 11 and thus catheters will adapt to the contours and curves of the surface of a patient's body (e.g., face) and will even adapt to conform to changes in the surface. Specifically, catheters 12 will be oriented in a downward fashion and move downward due to gravity. catheters 12 will experience an opposing upward force when contact is made with the patient, thereby conforming catheters to the surface of the patient.

Upon conforming catheters 12 to the surface of the patient's body and fixing the applicator guide in a reproducible position, a planning computed tomography (CT) scan will be performed through the applicator and the skin target to generate a CT data set. This CT data set will be used to generate a conformal radiation plan to treat the skin target. Radiation oncologist and medical physicist may adjust radiation dosing and treatment time using computing device 15 to control afterloader 14 to deliver the appropriate amount of radiotherapy to a patient. A radiation plan may be approved by a radiation oncologist. A healthcare professional may activate afterloader 14 via computing device 15 to deliver radiative material through transfer tubes 13 to a location within catheters 12 such as the tip.

Figure 2:
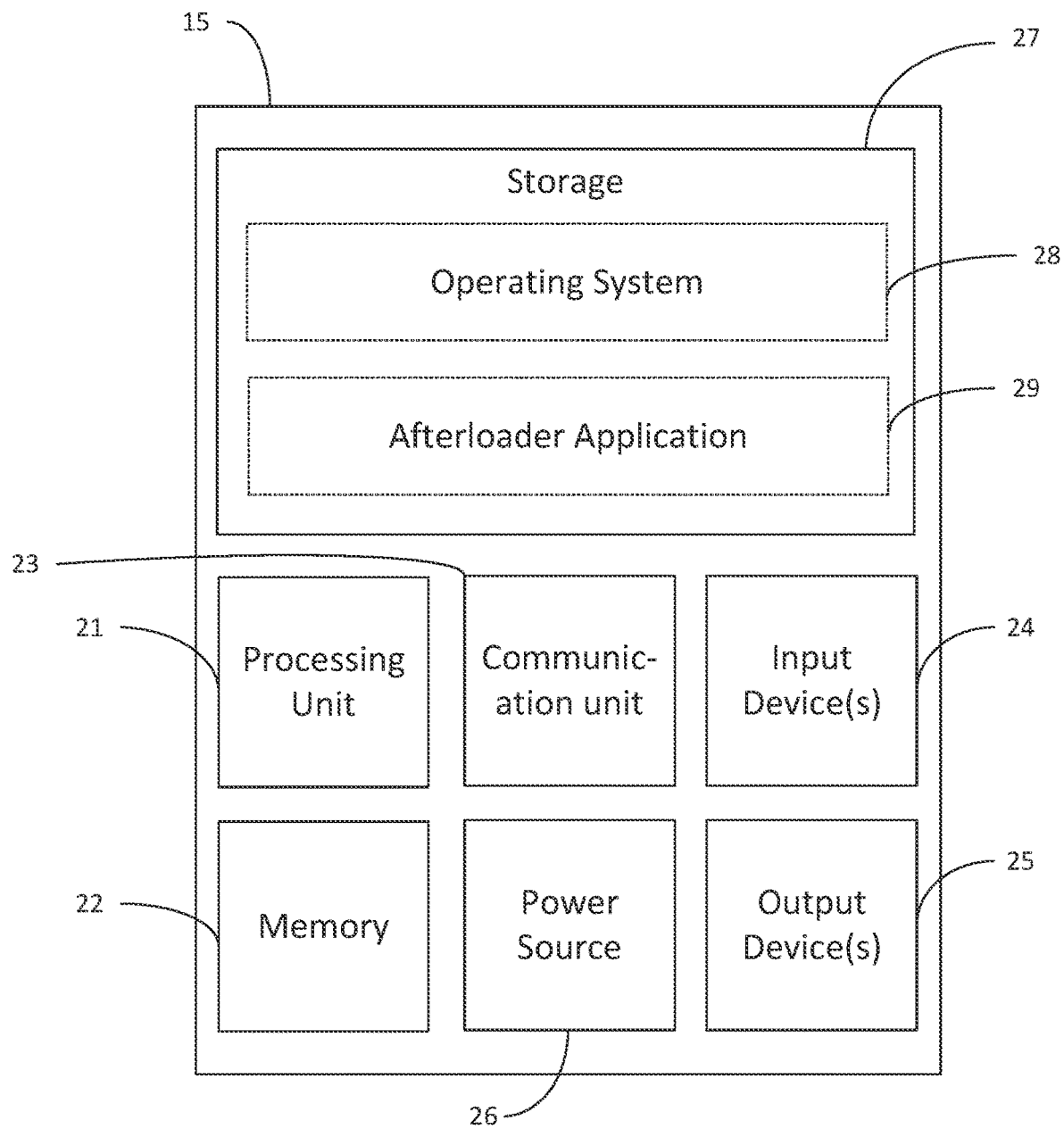
FIG. 2 is a schematic view of exemplary electronic and hardware components of the computing device.

Referring now to FIG. 2, exemplary functional blocks representing the hardware and software components of computing device 15 are shown. Hardware and software components of computing device 15 may include one or more processing unit 21, memory 22, storage 27, communication unit 23, and power source 26, input devices 24, and output devices 25. Computing device 15 may be in communication with the internet and/or other computing devices.

Processing unit 21 may be one or more processors configured to run operating system 28 and/or afterloader application 29. Afterloader application 29 running on processing unit 21 may control the operation of afterloader 14 and may otherwise implement oversee the operations and actions of afterloader 14. Afterloader application 29 may be stored in storage 27 and executed on processing unit 21. Afterloader application 29 may be a software application and/or software modules having one or more sets of instructions suitable for performing the operations of control computing device 15 set forth herein.

Computing device 15 may optionally run operating system 28 stored in storage 27 and executed on processing unit 21. Operating system 28 may be suitable for controlling the general operation of computing device 15 and may work together with afterloader application 29 to achieve the functionality of computing device 15 described herein. Computing device 15 may also optionally run a graphics library, other operating systems, and/or any other application programs.

Memory 22 may include, but is not limited to, volatile (e.g. random-access memory (RAM)), non-volatile (e.g. read-only memory (ROM)), flash memory, or any combination thereof. Communication unit 23 may receive and/or transmit information to and from other computing devices and/or peripheral devices. Communication unit 23 may be any well-known communication infrastructure facilitating communication over any well-known wired or wireless connection, including over any well-known standard such as any IEEE 802 standard. Power source 26 may be a battery or any other external source of power. Storage 27 may include, but is not limited to, removable and/or non-removable storage such as, for example, magnetic disks, optical disks, or tape.

Input device 24 may be one or more devices coupled to or incorporated into computing device 15 for inputting data to computing device 15. Input device 24 may include a keyboard, a mouse, a pen, a sound input device (e.g., microphone), a touch input device (e.g., touch pad or touch screen), and/or a camera, for example. Output device 25 may be any device coupled to or incorporated into computing device 15 for outputting or otherwise displaying data (e.g., display, speakers, printer, etc.).

It of course understood that computing device 15 may include additional or fewer components than those illustrated in FIG. 2 and may include more than one of each type of component.

Figure 3A:
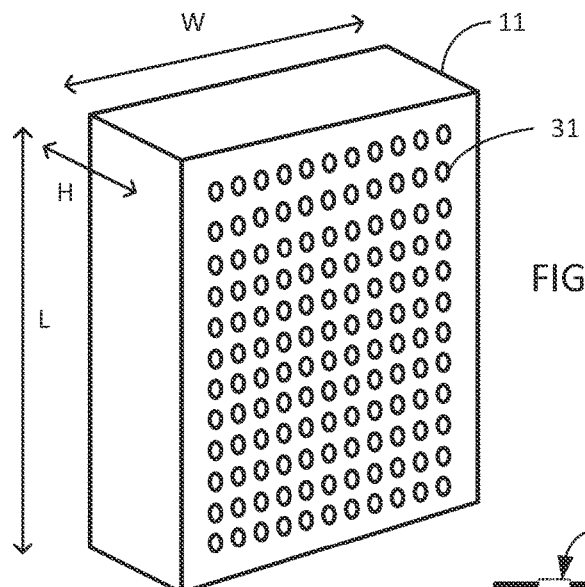
FIGS. 3A-3C illustrate perspective, side cross-sectional, and top views of an exemplary applicator guide.
Figure 3B:
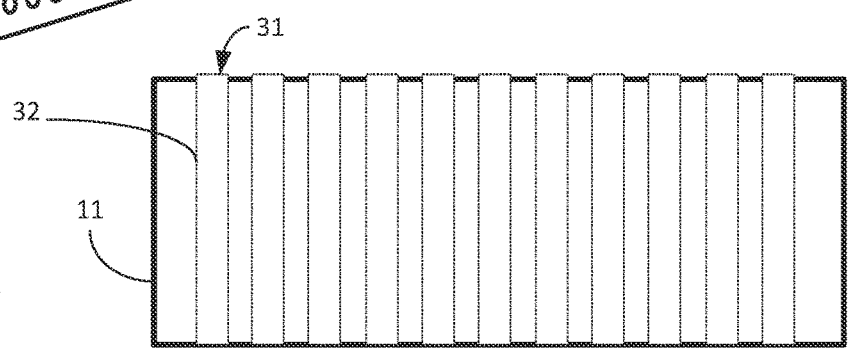
Figure 3C:
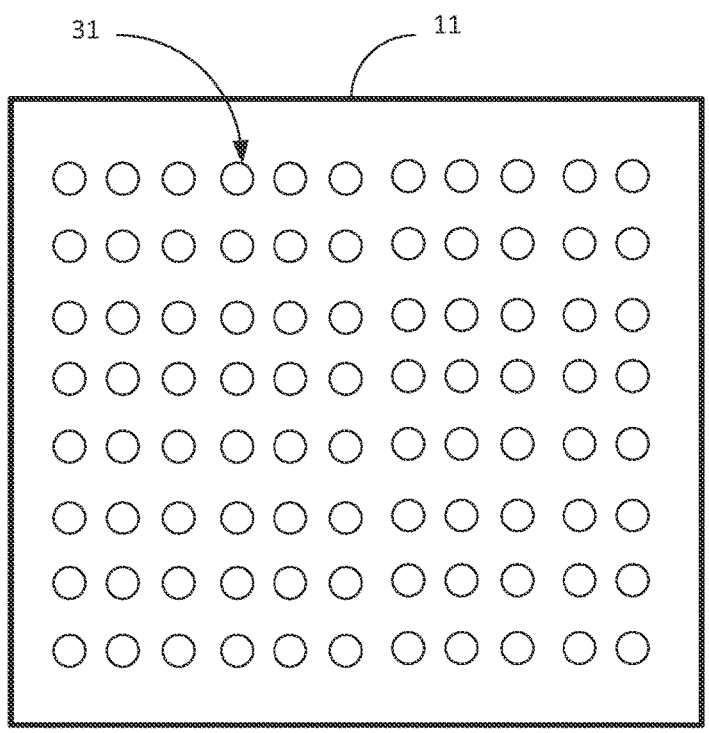

Referring now to FIGS. 3A-3C, applicator guide 11 is illustrated. Applicator guide 11 may be rectangular and have a plurality of through holes 31 and through hole channels 32 formed in an array that extend through the entire length of applicator guide 11 as shown in FIG. 3B. Applicator guide 11 may be hollow or may be solid with through holes extending through. Applicator guide 11 may have varying width W, length L, and height H dimensions and proportionality different than that shown in FIG. 3A while still accomplishing the functionality described herein. Applicator guide 11 has a height H that is large enough to maintain catheter 12 in an upright orientation as shown in FIG. 1B.

While applicator guide 11 is shown in FIG. 3A with a rectangular shape, it is understood that applicator guide 11 may take any other shape such as a circular or an asymmetric body. Through holes 31 may have a circular cross section with a constant radius. The radius may be sized such that catheters 12 fit within through hole channels 38 with enough clearance to move freely along through hole channel 38. Through hole channel 38 may have a smooth surface to reduce friction and may even be lined along a portion or the entire length of through hole channel 38 with a material different from applicator guide 11 to further reduce friction against catheters 12. Alternatively, through hole channels 38 may vary in radius or even shape. For example, through hole channels 38 may have a conical shape that narrows at one end. Applicator guide 11 may optionally include a lock at one or more through hole channels to lock catheters at a certain position within the through hole channel. For example, locks may include a screw or other protrusion that extends into the through hole channel and makes contact with the catheter to prevent the catheter from moving within the through hole channel. Locks may be activated together or individually.

The arrangement of through holes 31 that extend through applicator guide 11 may follow the generally uniform pattern illustrated in the top view of applicator guide 11 shown in FIG. 3C. The through holes may be closer together or further apart than those shown in FIG. 3C. Alternatively, the arrangement of through holes 31 may take on a different pattern or non-uniform pattern that that shown in FIG. 3C. Further, through holes 31 may vary in diameter and even shape to accommodate different shapes and sizes of catheters 12. For example, through holes 31 near the center of applicator guide 11 may have a larger diameter than through holes 31 that are located near the perimeter of applicator guide 11. In yet another alternative arrangement, through holes 31 may be positioned closer to one another near the center of applicator guide 11 and further from one another near the perimeter of applicator guide 11.

Figure 4A:
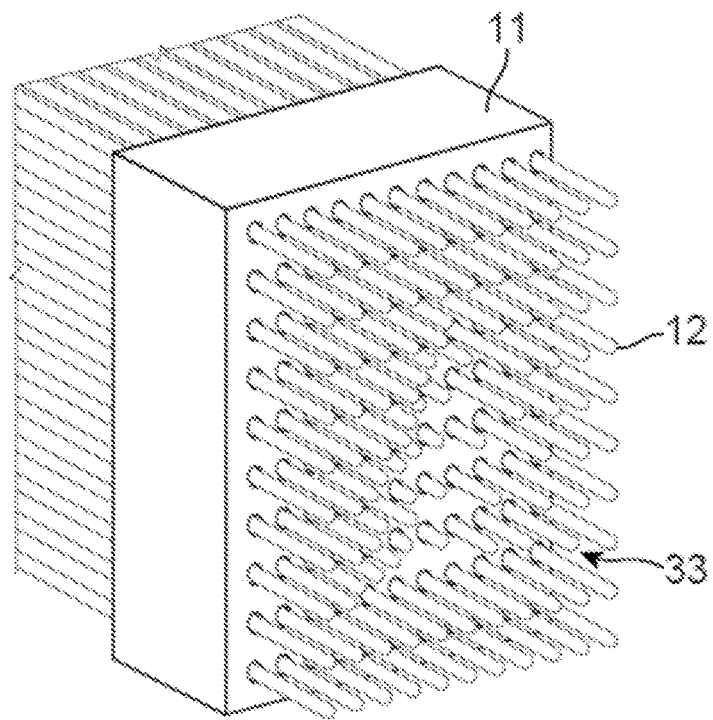
FIG. 4A is a perspective view of an exemplary applicator guide loaded with catheters.

Referring now to FIG. 4A, applicator guide 11 is shown with catheters 12 loaded into each through hole 31 of applicator guide 11. The combination of applicator guide 11 with catheters 12 is referred to herein as an applicator assembly. In this example, a triangular imprint is visible in the catheters. This shape may be the result of applicator guide 11 and catheters 12 positioned over a patient's nose as shown in FIG. 1B. As each catheter 12 is free to move independent along each through hole 31 channel, each catheter may conform to the surface that it comes in contact with. When applicator guide is placed in the orientation illustrated in FIG. 1B, catheters will be free to move along the through hole channels and ultimately conform to the patient's nose resulting in triangular imprint 33 shown in FIG. 4A. While a triangular shape is illustrated in FIG. 4A, applicator guide 11 may conform to any other shape.

Figure 4B:
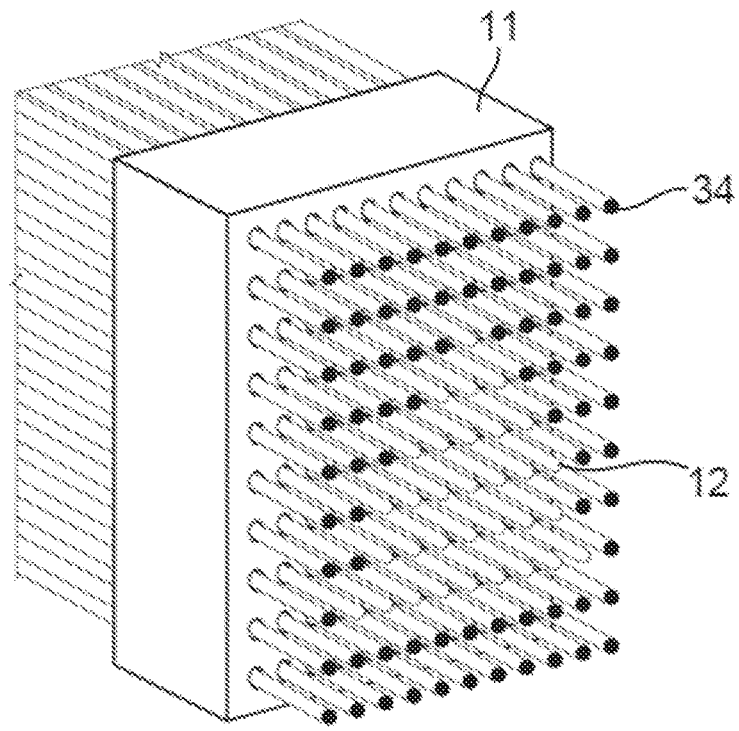
FIG. 4B is a perspective view of an exemplary applicator guide loaded with catheters and tungsten inserts.

Referring now to FIG. 4B, applicator guide 11 is illustrated. Unlike FIG. 4A, catheters 12 connected to afterloader 14 and designed to receive the radioactive source may occupy only some of through holes 31. The other through holes in FIG. 4B may be occupied by shield inserts 34 having a shape similar to catheters 12 but designed to move freely within though hole 31 channels. Catheters 12 will carry radioactive sources and thus deliver radiotherapy to a patient. They may be inserted at specific through hole 31 locations throughout applicator guide 11. The location of catheters 12 may be selected to deliver radiotherapy to only a localized area of the surface of a patient's skin—the target. Shield inserts 34 may be a made from a material that protects against radiation such as tungsten, or any other material exhibiting similar qualities. Accordingly shield inserts 34 may surround catheters 12 as shown in FIG. 4B to block radiation scatter from uninvolved skin outside of the skin radiation target.

Figure 5:
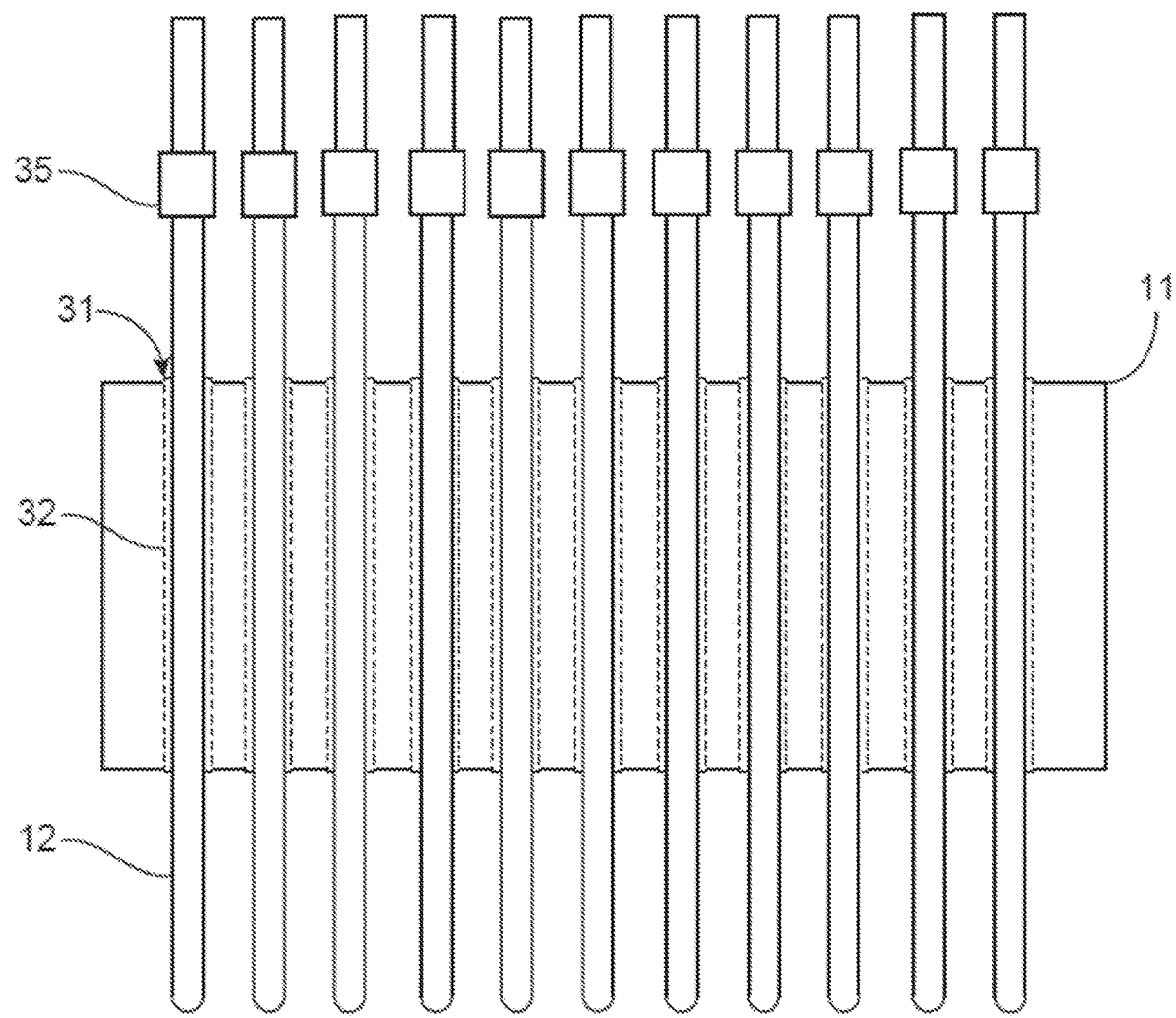
FIG. 5 is a cutaway view of an exemplary applicator guide with a stoppers attached and positioned in an applicator guide.

Referring now to FIG. 5, a cross-sectional view of applicator guide 11 is illustrated. Catheters 12 may extend through each through hole channel 32. As shown in FIG. 5, each catheter 12 may include stopper 35 which may be coupled to an exterior surface of catheter 12. Stopper 35 may be a protrusion that extends beyond the diameter of catheter 12 and may extend 360° around catheter 12 or only a portion. Coupled to stopper 35, catheter 12 will be prevented from extending down into through hole channel 32 beyond stopper 35 as stopper 35 will not fit inside through hole channel 32. This may be desirable to prevent catheters 12 from falling completely though applicator guide 11 and/or otherwise limiting the allowable movement of catheters 12. It may be further desirable to include a second stopper below through hole channel 32 to prevent catheters 12 from exiting applicator guide 11 from the other direction, and thus further liming the range of movement of catheters 12.

Figure 6A:
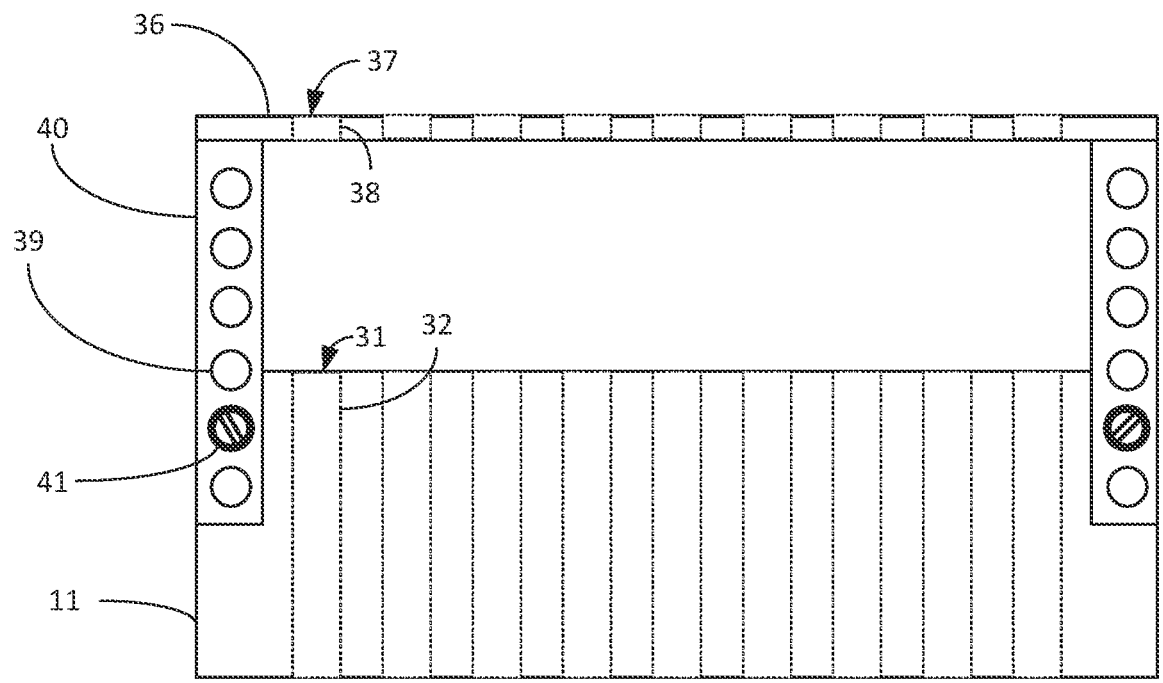
FIGS. 6A and 6B illustrates side and top views of an exemplary applicator guide with an exemplary guide extension.
Figure 6B:
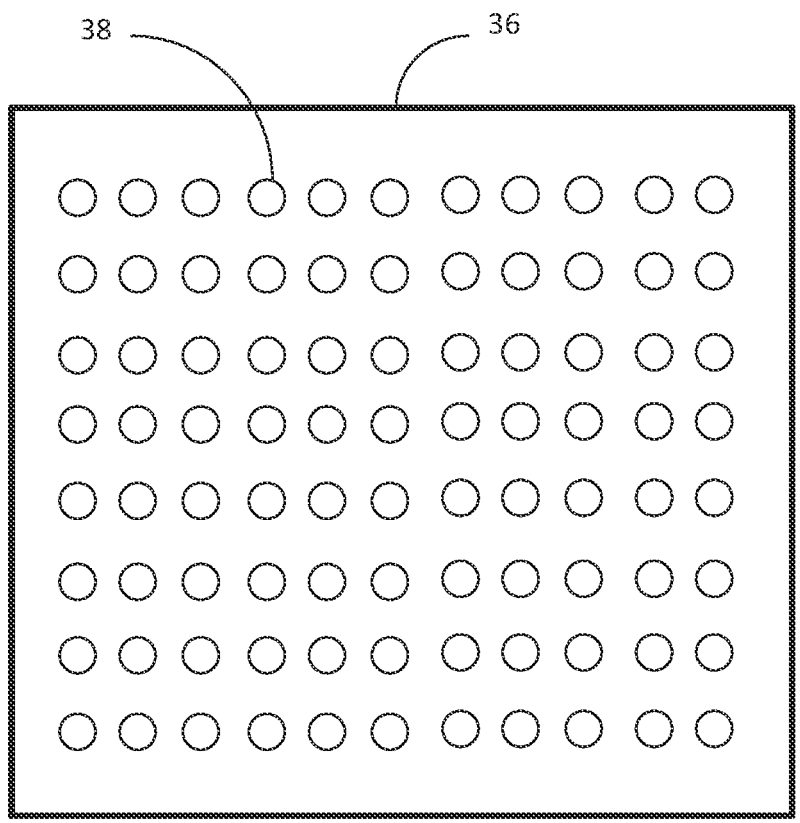

As is shown in FIG. 6A, applicator guide 11 may include guide extension 36. Guide extension 36 may be removably coupled to applicator guide 11 via legs 40 to provide increased stability for catheters 12. Guide extension 36 may have a plurality of through holes 31 and corresponding through hole channels 38 that extend though guide extension 36 and align with through holes 31 and through hole channels 32. FIG. 6B is an exemplary top view of guide extension 36 having through holes 31. Accordingly, catheters 12 and/or shield inserts 34 may be positioned through guide extension 36 and applicator guide 11.

Guide extension 36 may be positioned a certain height above applicator guide 11 via legs 40. The distance between guide extension 36 and applicator guide 11 may be adjusted. In the example shown in FIG. 6A, guide extension 36 may include several screw holes 39 in legs 40 through which screws 41 may be inserted. Applicator guide 11 may include threaded portions (not shown) into which screws 41 may screw into to secure guide extension 36 into place. In this manner, the distance between guide extension 36 and applicator guide 11 may be adjusted by placing screw 41 into a different screw hole 39. It is understood, however, that different adjustment structures may be used to adjust the height of guide extension 36. For example, guide extension 36 may be coupled to applicator guide 11 via a rail system upon which guide extension 36 may slide up and down and lock into place (e.g., using a screw or latch). In another example, guide structure may be permanently coupled to applicator guide 11 or may be formed from the same piece.

Figure 7:
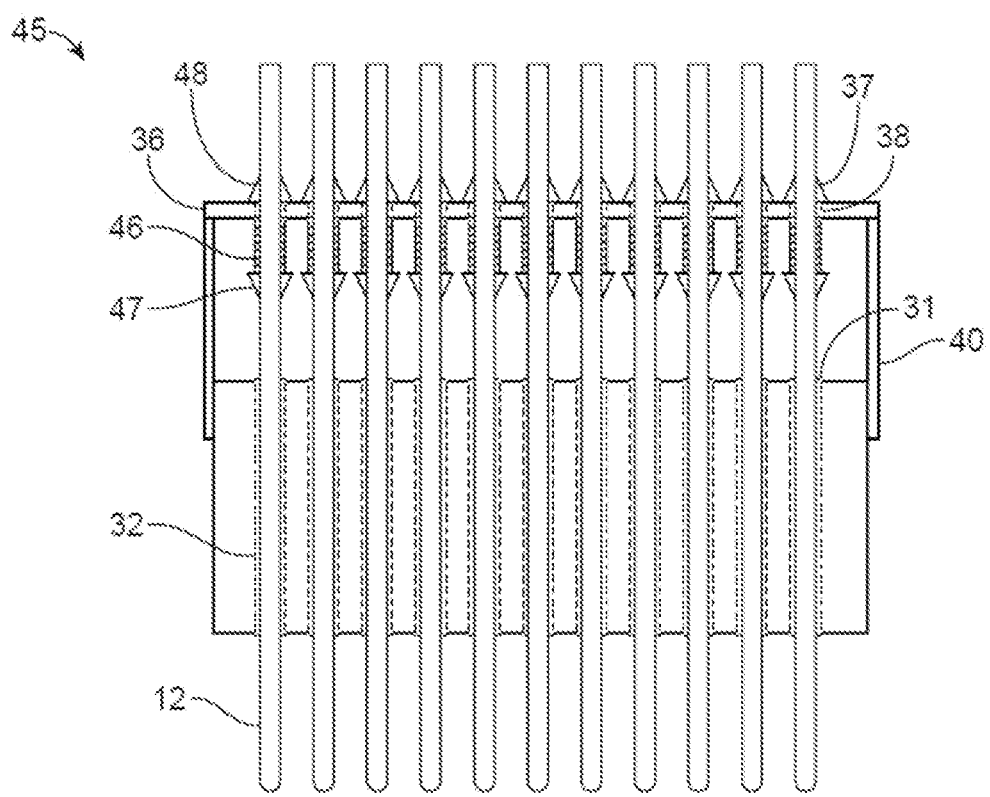
FIG. 7 illustrates an exemplary applicator guide with a guide extension having springs and loaded with catheters.

Referring now to FIG. 7, spring assembly 45 is illustrated. Spring assembly 45 is includes applicator guide 11 and guide extension 36. Further, spring assembly 45 may include springs 46 aligned with through hole channels 38, each spring 46 may have elastic properties such that it may compress to a length shorter than its neutral length when a compressive axial force is applied and return to its neutral length when the force is removed. Each spring 46 may have an interior void sized such that catheters 12 and/or shield inserts 34 may move freely within springs 46. For example, springs 46 may have the same interior diameter as through hole channel 38 and through hole channel 32.

Springs 46 may be coupled to guide extension 36 on an underside of guide extension 36. Alternatively, springs 46 may sandwiched between guide extension 36 and lower protruders 47. Lower protruders 47 may extend from catheters 12 and may be sized and shaped such that they prevent springs 46 from extending over lower protruders 47. As shown in FIG. 7, lower protruders 47 may be triangular in shape though they may be any other shape the prevents springs 46 from extending over. It may be desirable for lower protruders 47 to retract into catheters 12 to permit lower protruders 47 to fit inside through hole channels 38 of guide extension 36.

Catheters 12 may further include upper protruders 48. Upper protruders 48 may extend from catheters 12 and may be sized and shaped such that they prevent catheter 12 from extending inside through hole channels 38. As shown in FIG. 7A, upper protruders 46 may be triangular in shape, however it is understood that upper protruders 48 may take any other shape that prevents catheters 12 from traversing through hole channels 38. It is understood that while upper protruders 48 serve to restrict movement of catheters 12 and prevent catheters 12 from extending beyond a certain point, upper protruders 48 are optional in that they are not needed for springs 46 to achieve their intended functionality described herein.

Spring assembly 45 may be used to limit the range of motion of catheters 12. Spring assembly 45 may be positioned to deliver therapy to a patient, similar to the orientation shown in FIG. 1B. As described above with respect to FIG. 1B, catheters 12 will make contact with the surface of the patient (e.g., the face of the patient). Catheters 12 will thus experience an opposing upward force when contact is made with the surface of the patient. The upward force will cause catheters to move upward toward applicator guide 11 and guide extension 36.

As catheters 12 move upward, lower protruding portion will also move upward toward guide extension 36. As guide extension 36 remains stationary, the upward movement of lower protruders 47 will cause springs 46 to compress. At a certain point, springs 46 will no longer be able to compress. Accordingly, spring 46 will define a range of motion of catheters 12 in that catheters 12 may be permitted to travel upwards the distance between a neutral length of the spring and a fully compressed length of the spring. Spring assembly 45 provides improved control over the movement of catheters and thus the distribution of radiotherapy.

Figure 8:
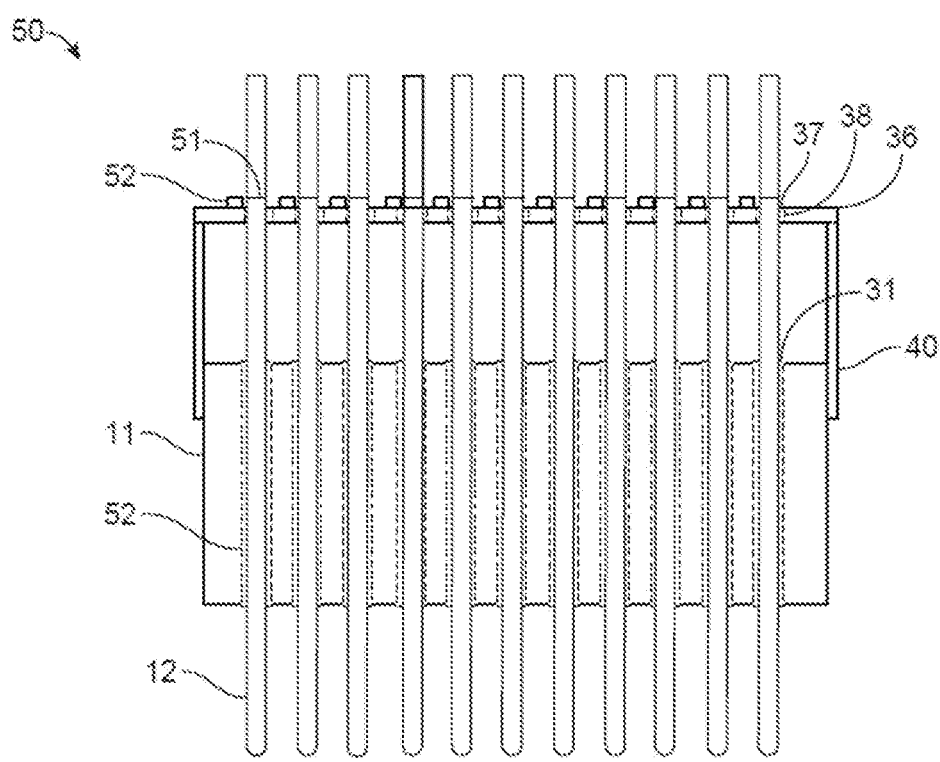
FIG. 8 illustrates an exemplary applicator guide with a guide extension having sensors and loaded with catheters.

Referring now to FIG. 8, sensor assembly 50 is illustrated. Sensor assembly 50 includes at least applicator guide 11 and guide extension 36. Sensor assembly 50 may further include reference identifiers 51 and sensors 52. Sensors 52 may be installed on guide extension 36 near through holes 31. Sensors 52 sense the position of reference identifiers 51 and may determine if reference identifier 51 is beyond a threshold distance from sensor 52. Sensors 52 may communicate and/or otherwise interface with reference identifiers 51 via a wired or wireless communications. For example, sensor 52 may be a photoelectric sensor. Alternatively, sensor 52 may be any other well-known wired or wireless sensor designed to determine the position of catheter 12 and/or reference identifier 51.

Applicator guide 11 and/or guide extension 36 may be coupled to or otherwise house a power source such as a battery to supply power to sensors 52. Applicator guide 11 and/or guide extension 36 may also include a transceiver in communication with sensors 52. Alternatively, sensors 52 may each include a transceiver. Sensors 52 may communicate via the transceiver with computing device 15 via any well-known wireless connection (BlueTooth, Wi-Fi, etc.). Alternatively, sensors 52 may communicate with computing device 15 via a wired connection.

Sensors 52 may determine the distance reference identifier 51 is displaced from sensor 52 or some other neutral position. Sensor 52 may then communicate this information to computing device 15. Each sensor may correspond to a specific catheter. Computing device 15 may run afterloader application 29 which may use this information to selectively deliver radioactive material to certain catheters.

In one example, afterloader application 29 may analyze data received from sensors 52 and determine that several catheters moved beyond a certain threshold distance. For example, sensors 52 may produce data that suggests that several of the catheters moved a significant distance in response to contact with the patients nose. A healthcare provider may be targeting the nose or a portion thereof and thus may instruct afterloader 14 to only deliver radioactive material to the catheters that have moved a certain distance.

Figure 9:
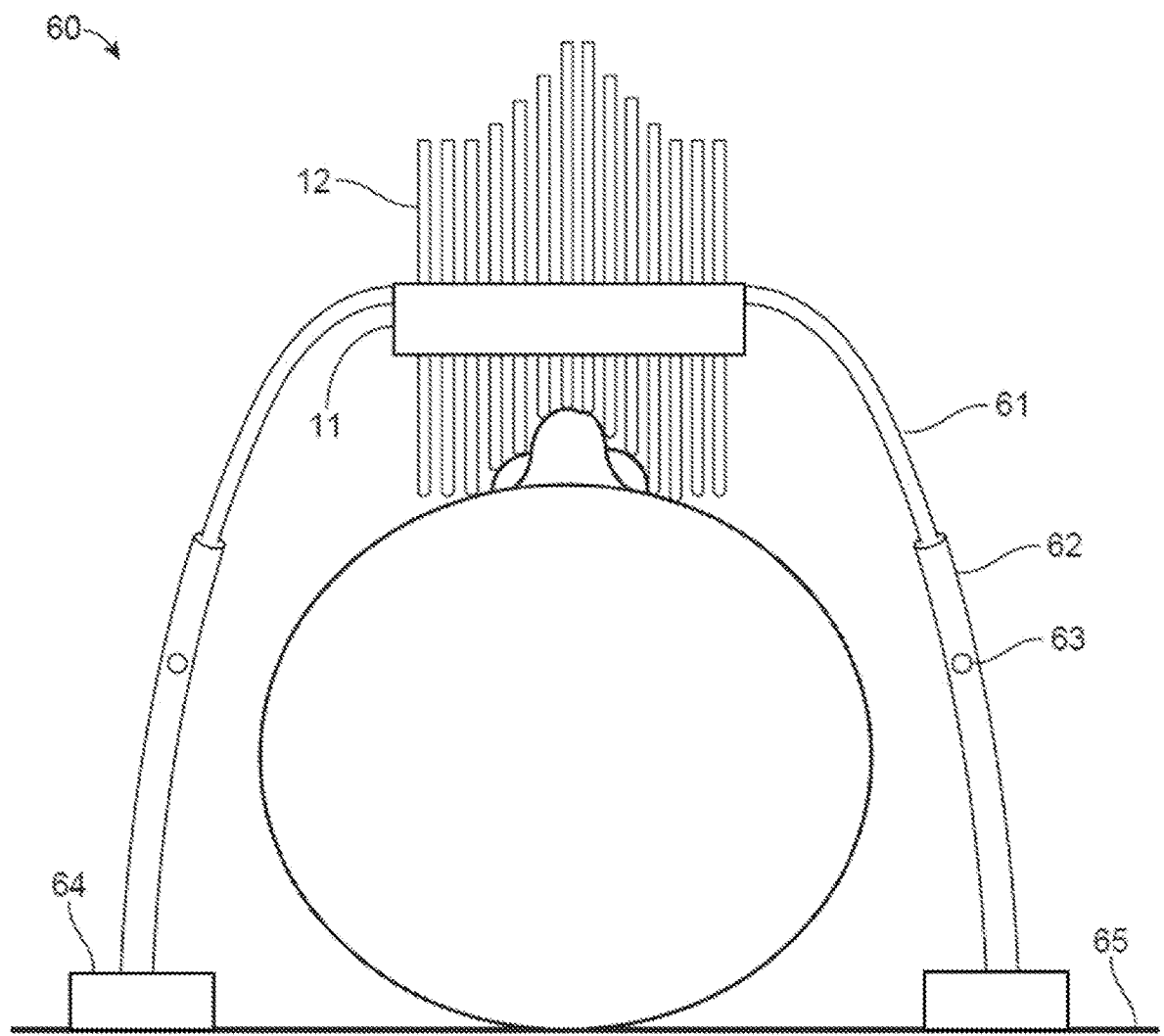
FIG. 9 illustrates an exemplary applicator guide coupled to a table mount and positioned over the face of a patient.

Referring now to FIG. 9, applicator guide 11 loaded with catheters 20 may be positioned over a desired portion of the patient's anatomy. While applicator guide 11 is illustrated positioned over the patient's face in FIG. 9, it is understood that applicator guide could be positioned over any other portion of the patient's anatomy such as a leg or arm. To hold applicator guide 11 in place over the targeted anatomical area, applicator guide 11 may be secured to table mount 60 which rests on table 65.

To use table mount 60, the patient must be positioned on a table (e.g., operating table) or other generally flat surface (e.g., bed). Table mount 60 may include at least two mount arms 61 coupled to mount stabilizers 64 which sit on the generally flat surface. Mount stabilizers 64 generally maintain table mount 60 and thus applicator guide 11 in a stable position and may even be screwed into or otherwise affixed to the generally flat surface.

Figure 10:
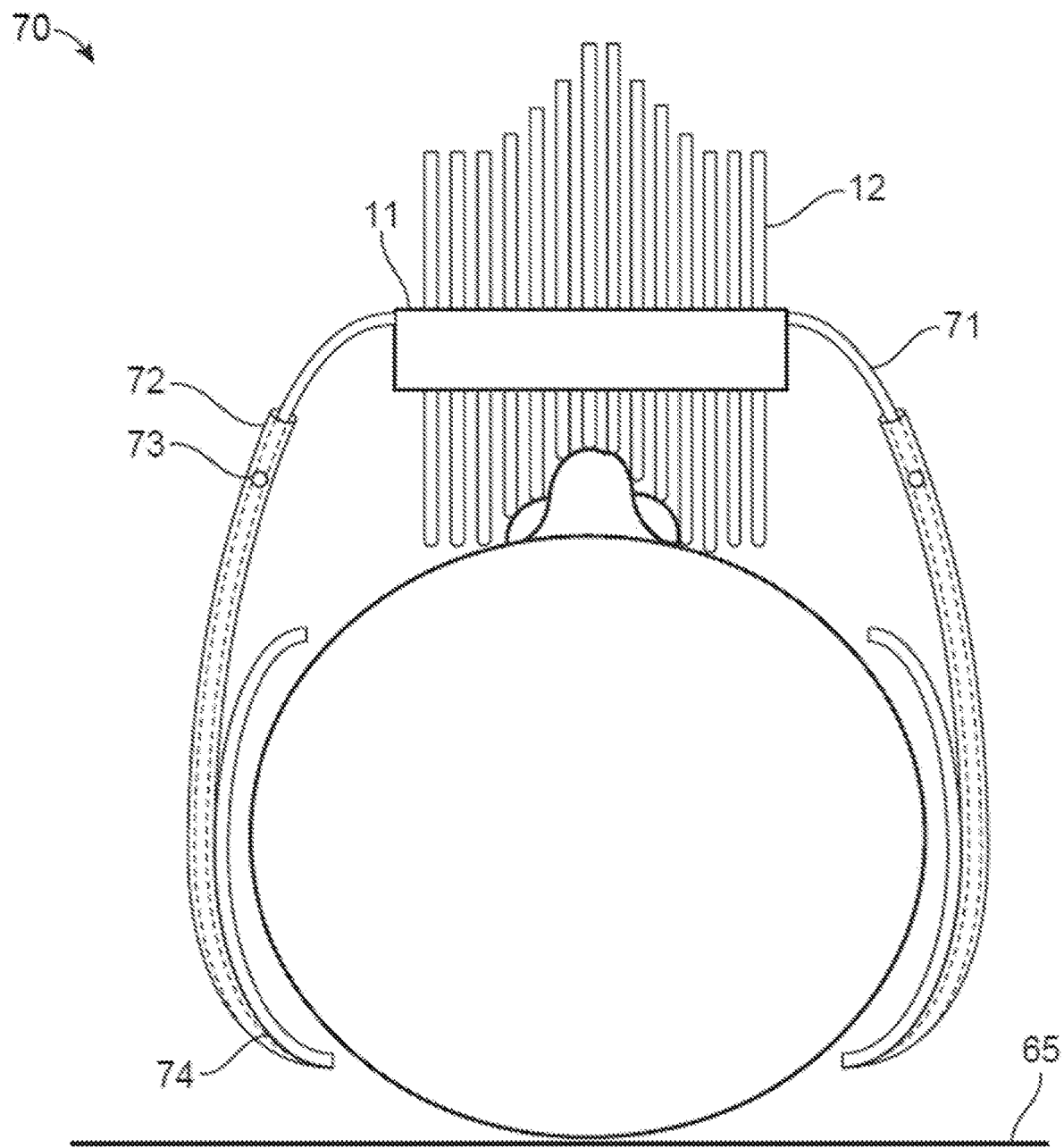
FIG. 10 illustrates an exemplary applicator guide coupled to a head mount and positioned over the face of a patient.

Mount arms may be coupled to and secured to mount stabilizers 64. Mount arms 61 may extend up from mount stabilizers and couple to applicator guide 11. Mount arms 61 may be include arm extenders 62 which may be movably coupled to mount arms 61. For example, as shown in FIG. 10, and each mount arm 61 may extend into a respective arm extender 62 and each arm extender 62 may include engagement button 63 to lock mount arm 61 at a certain position along arm extenders 62. Engagement button 63 may be a spring loaded protrusion that extends into mount arm 61 or otherwise locks mount arm 61 into place. Engagement button 63 may be used to extend mount arms 61 and thus raise or lower applicator guide 11.

Mount arms 61 may be removably coupled to applicator guide 11 via any well-known coupling technique. For example mount arms 61 may be coupled to applicator guide 11 via threaded screws that are received by a threaded receiving portion inside of applicator guide 11. In another example, applicator guide 11 may snap into place. Alternatively, table mount 60 may be permanently coupled to applicator guide 11. Table mount 60 secures applicator guide 11 such that the catheters 12 are oriented in a generally upright position. In this orientation, catheters 12 may freely move downward and traverse through hole channels 32.

Referring now to FIG. 10, applicator guide 11 loaded with catheters 20 may be positioned over a portion of a patient's head via head mount 70. For example, applicator guide 11 may be positioned over a portion of a patient's face. In another example, applicator guide 11 may be positioned over a different portion of the patient's head, such as an ear. To hold applicator guide 11 in place over the targeted anatomical area, applicator guide 11 may be secured head mount 70 which is secured to the head of the patient.

Head mount 70 may include at least two mount arms 71, each coupled to a respective head stabilizer 74 that is secured to a patient's head. Mount arms 71 may extend up from head stabilizers 74 and couple to applicator guide 11. Mount arms 71 may be include arm extenders 72 which may be movably coupled to mount arms 71. For example, as shown in FIG. 10, each mount arm 71 may extend into a respective arm extender 72 and each arm extender 72 may include engagement button 73 to lock mount arm 71 at a certain position along arm extenders 72. Engagement button 73 may be a spring loaded protrusion that extends into mount arm 71 or otherwise locks mount arm 71 into place. Engagement button 73 may be used to raise or lower mount arms 71 and thus applicator guide 11.

Head stabilizers 74 may be secured to the patients head via compression pressure. Mount arms 71 and/or arm extenders 72 may be made from elastic material and may be stretched from a neutral position when secured to the head of the patient, resulting in the compressive force. Alternatively, or in addition to, head stabilizers 74 may be strapped to a patient's head via a strap such as a Velcro strap, elastic headband, or other well-known approaches. Head stabilizers 74 may include a padded portion for contacting the head of the patient.

Mount arms 71 may be removably coupled to applicator guide 11 via any well-known coupling techniques. For example mount arms 71 may be coupled to applicator guide 11 via threaded screws that are received by a threaded receiving portion inside of applicator guide 11. In another example, applicator guide 11 may snap into place. Alternatively, head mount 70 may be permanently coupled to applicator guide 11 or be formed from the same piece.

Head mount 70 secures applicator guide 11 such that the catheters are oriented in the same position with respect to the head of the patient. The head of the patient may be strapped down to table 65 to maintain the patient's head in a constant orientation. Head mount 70 is preferably oriented upon the patient such that catheters 12 are in a generally upright position and catheters 12 are free to move downward and traverse through hole channels 32.

Figure 11:
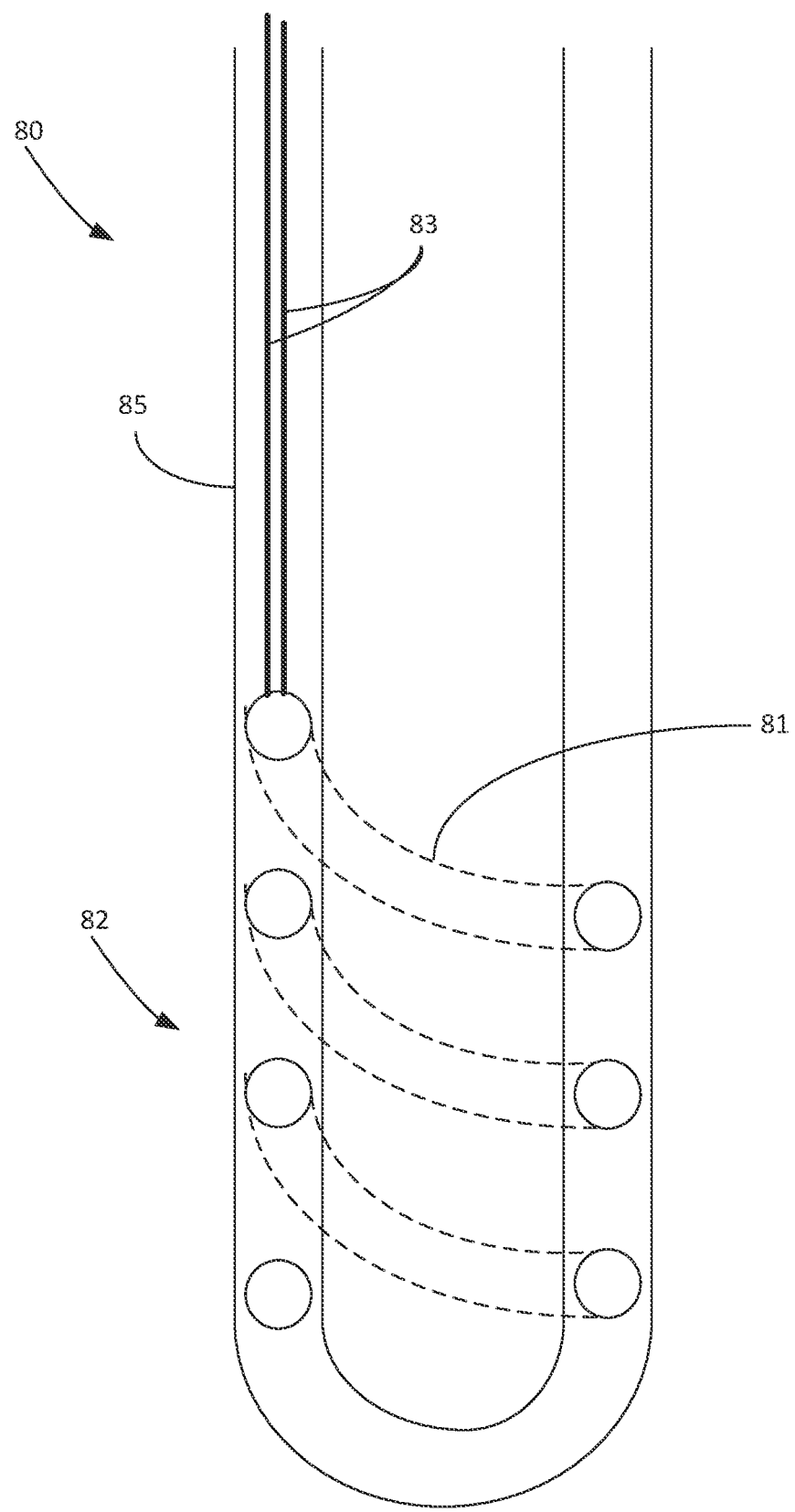
FIG. 11 is a cutaway view of an exemplary catheter with a heater.

Referring now to FIG. 11, an optional hyperthermia catheter is illustrated. As combining radiotherapy with hyperthermia has been observed to increase cancer cell kill and curability rates, it may be desirable to combine a traditional radiotherapy catheter with a hyperthermia needle. For example, hyperthermia catheter 80 may have similar functionality and structure as catheter 12 but may further include heater 81 along at least a portion of catheter 80. As is shown in FIG. 11, heater 81 may be positioned in walls 85 of distal end 82 of catheter 80 such that heat is applied to the targeted tissue of the patient when distal end 82 of catheter 80 is near the targeted tissue. Heater 81 may be electrically insulated from catheter 80.

Heater 81 may be connected via circuitry 83 to a power source (not shown) which may be in electrical communication with computing device 15. Computing device 15 may run afterloader application 29 or a standalone application to selectively activate heater 81 to heat the targeted tissue. Circuitry may be connected to an independent power source or may use a power source integrated into afterloader 14. The healthcare professional using computing device 15 may select all catheters or only select certain catheters for applying heat. Alternatively, afterloader application 29 may automatically apply power to certain catheters based on data received from sensors and/or according to programmed instructions.

While FIG. 11 illustrates catheter 80 having a heating coil, it is understood that heater 81 may employ any other well-known heating technique. For example, heater 81 may be a radio frequency (RF) electrode. Alternatively, heater 81 may be one or more fluid channels within walls 85 of catheter 80 and heated fluid may be introduced to the one or more fluid channels to apply heat to the targeted tissue.

Figure 12:
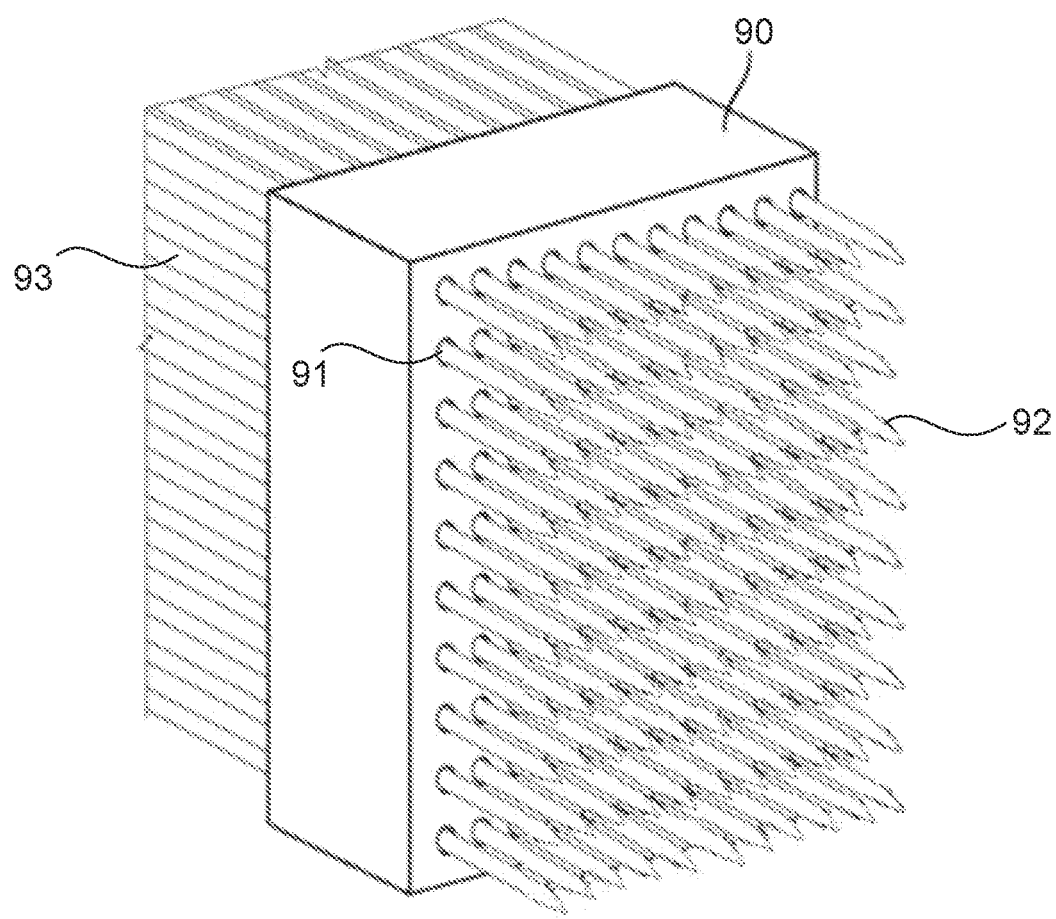
FIG. 12 is a perspective view of an exemplary applicator guide loaded with microneedles.

The systems and methods described herein for delivering and guiding applicators to non-uniform surfaces in a manner to permit catheters to conform to curved surfaces and even adapt to dynamic surfaces may be used for transdermal application of therapy to dynamic skin surfaces. Referring now to FIG. 12, applicator guide 90 for transdermal application of therapy is provided. Applicator guide 90 may be constructed similar to applicator guide 11 of FIGS. 4A and 4B, except that through hole channels 91 of applicator guide 90 are sized and shaped to receive microneedles 92 therethrough, such that microneedles 92 fit within through hole channels 91 with enough clearance to move freely along through hole channel 91. Each of microneedles 91 have a distal tip configured to non-invasively penetrate at least the stratum corneum (SC) of the patient's skin. In addition, each of microneedles 92 may be coupled to transfer tubes 93 extending from microneedles 92 to a source of therapy, e.g., drug reservoir, ultrasound transducer, or RF energy source, such that the therapy may be applied to the patient via microneedles 92 and transfer tubes 93. A computing device may be operatively coupled to the source of therapy to selectively administer the therapy.

Microneedles 92 are free to move within applicator guide 90, and thus microneedles 92 will adapt to the contours and curves of the surface of a patient's body, and will even adapt to conform to changes in the surface. Microneedles 92 may be oriented in a downward fashion and may move downward due to gravity. Accordingly, microneedles 92 will experience an opposing upward force when contact is made with the surface of the patient's skin, thereby conforming microneedles 92 to the surface of the patient in a conformed orientation. Microneedles 92 may also be oriented in other directions, such that application of a force on applicator guide 90 toward the patient's skin causes a reaction force against microneedles 92 when contact is made with the surface of the patient's skin.

Applicator guide 90 includes a lock at one or more through hole channels 91 to lock microneedles 92 at a certain position within through hole channel 91, e.g., in the conformed orientation. For example, locks may include a screw or other protrusion that extends into through hole channels 91 and makes contact with microneedles 92 to prevent microneedles 92 from moving within through hole channels 91. The locks may be activated together or individually.

When microneedles 92 are locked in the conformed orientation relative to applicator guide 90, a force may be applied to applicator guide 90 toward the patient's skin, such that microneedles 92 non-invasively penetrate the patient's skin with uniform pressure and to a relative uniform depth, taking into account the contours and curves of the surface of the patient's body. Accordingly, microneedles 92 may deliver therapy to the patient transdermally.

In some embodiments, microneedles 92 and applicator guide 90 may be used to deliver drug therapy to the patient transdermally. For example, microneedles 92 may be coated with a drug, such that the drug is delivered to the patient upon penetration of the patient's skin with microneedles 92. Alternatively, microneedles 92 may be embedded with the drug, and may further be dissolvable, e.g., by application of heat to microneedles 92 either actively by the system or naturally by the patient's body. Accordingly, when microneedles 92 are positioned within the patient's skin, microneedles 92 may be dissolved to deliver the drug transdermally. In another embodiment, microneedles 92 may be used to non-invasively penetrate the patient's skin, and then removed via applicator guide 90, leaving micro-incisions within the patient's skin. Accordingly, a topical drug may then be administered to the micro-incisions such that the drug may penetrate the stratum corneum barrier and reach the target area within the patient's skin.

Figure 13:
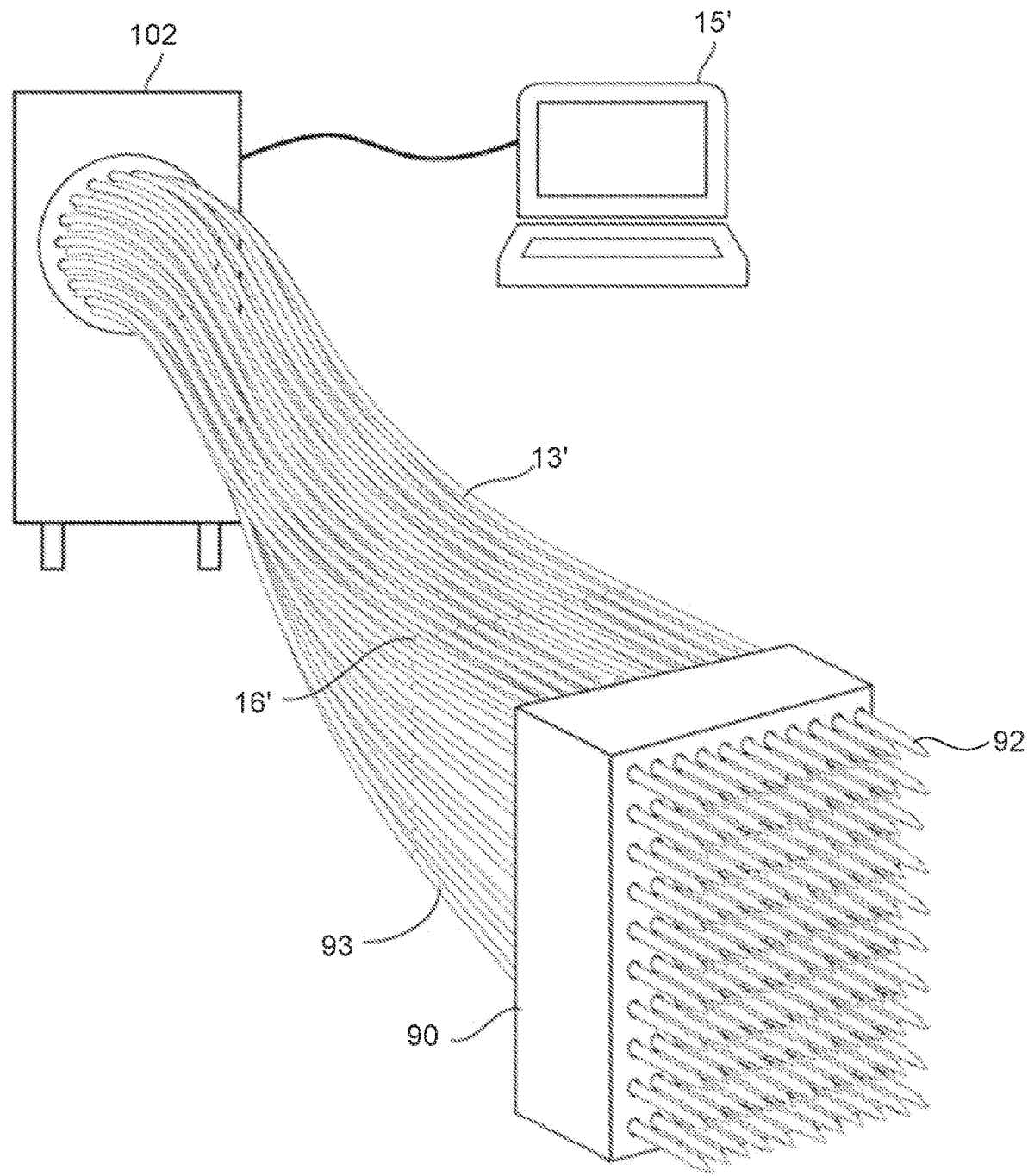
FIG. 13 illustrates the therapy system including the drug reservoir, applicator guide, and computing device for delivering a drug transdermally.

Alternatively or additionally, microneedles 92 may be hollow, e.g., having a lumen extending through the distal tip of microneedles 92, the lumen in fluid communication with transfer tubes 93. Accordingly, as shown in FIG. 13, transfer tubes 93 may be coupled to drug reservoir 102, e.g., via connecting interface 16' and transfer tubes 13', such that the drug may be delivered from drug reservoir 102, through transfer tubes 13' and transfer tubes 93, and through the distal end of microneedles 92 into the target area within the patient's skin, transdermally.

Computing device 15' may be a standalone computing device, or may be incorporated into drug reservoir 102. Drug reservoir 102 may include a pump mechanism for delivering the drug from drug reservoir 102 through transfer tubes 13'. Computing device 15' may communicate with drug reservoir 102 via any well-known wired or wireless connection (BlueTooth, Wi-Fi Direct, etc.). The clinician may adjust drug dosing and treatment time using computing device 15' to control drug reservoir 102 to deliver the appropriate amount of the drug to a patient.

In some embodiments, the applicator guides described herein may be used to deliver energy percutaneously and/or transdermally to the target area within the patient's skin via the plurality of transfer tubes, catheters, and/or microneedles. For example, the applicator guide may be used to percutaneously and/or transdermally deliver radiofrequency (RF) energy, ultrasound energy, or laser energy to the target area on/within the patient's skin.

Figure 14:
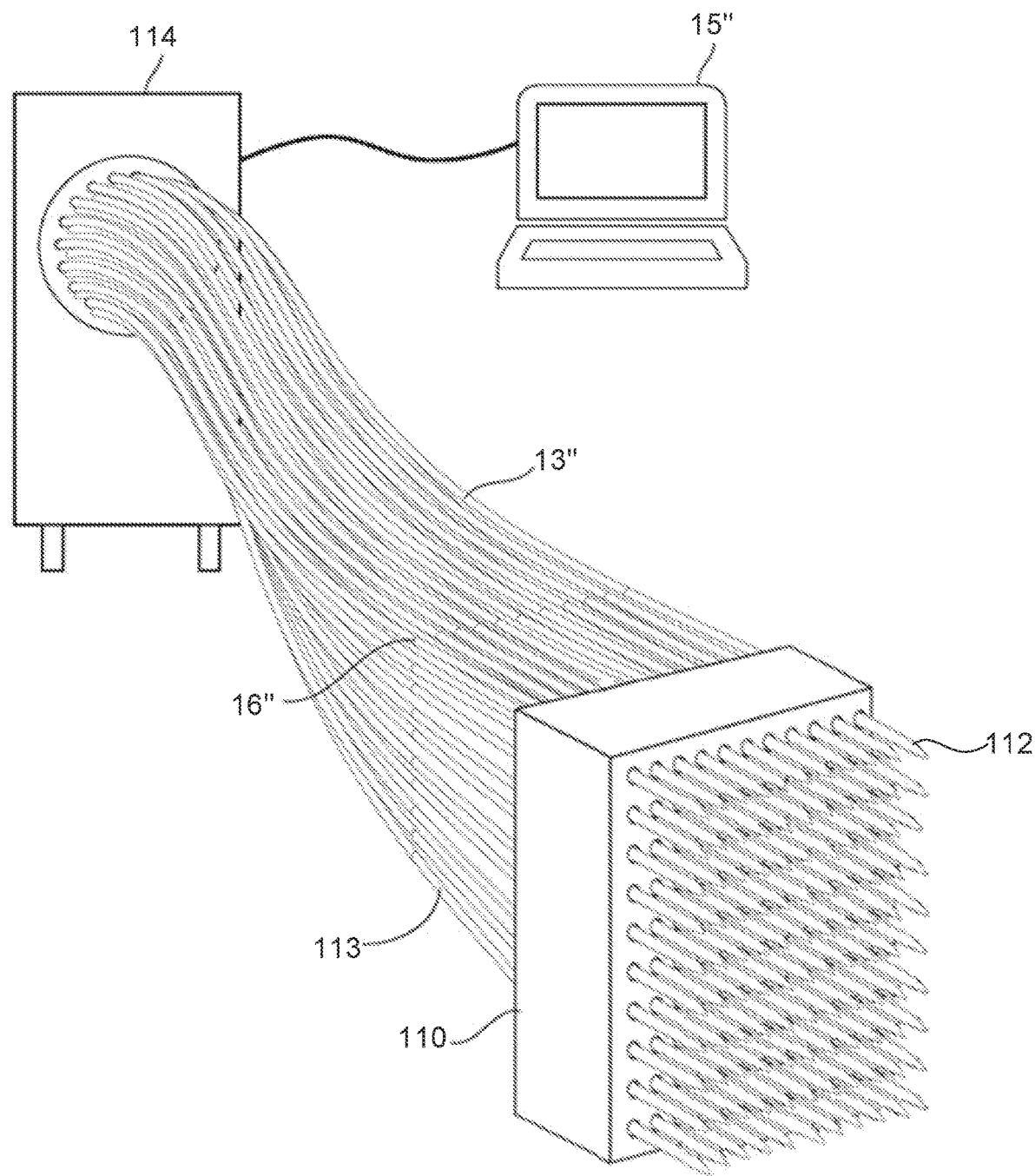
FIG. 14 illustrates the therapy system including the pulse generator, applicator guide, and computing device for delivering RF energy.

As shown in FIG. 14, the distal end of transfer tubes 113 may be needle-like electrodes 112, electrically coupled to pulse generator 114. Transfer tubes 113 may be coupled to pulse generator 114 via transfer tubes 13" and connecting interface 16". Computing device 15" may be a standalone computing device, or may be incorporated into pulse generator 114. Pulse generator 114 may be programmed to deliver RF energy to the target area on/within the patient's skin sufficient to ablate the target tissue. For example, needle-like electrodes 112 may be guided by applicator guide 110 to conform to the contours of the patient's skin at the target area, such that RF energy may be uniformly delivered to the target tissue.

Alternatively, pulse generator 114 may be programmed to deliver RF energy to the target area within the patient's skin (e.g., sufficient for depigmentation such as tattoo removal). Accordingly, needle-like electrodes 112 may be locked into place relative to applicator guide 110, and may non-invasively penetrate a stratum corneum (SC) of the patient's skin to deliver RF energy within the patient's skin at the target area. Computing device 15" may communicate with pulse generator 114 via any well-known wired or wireless connection (BlueTooth, Wi-Fi Direct, etc.). The clinician may adjust RF energy emission and treatment time using computing device 15" to control pulse generator 114 to deliver the appropriate amount of the RF energy to a patient, e.g., for ablation and/or depigmentation.

Figure 15:
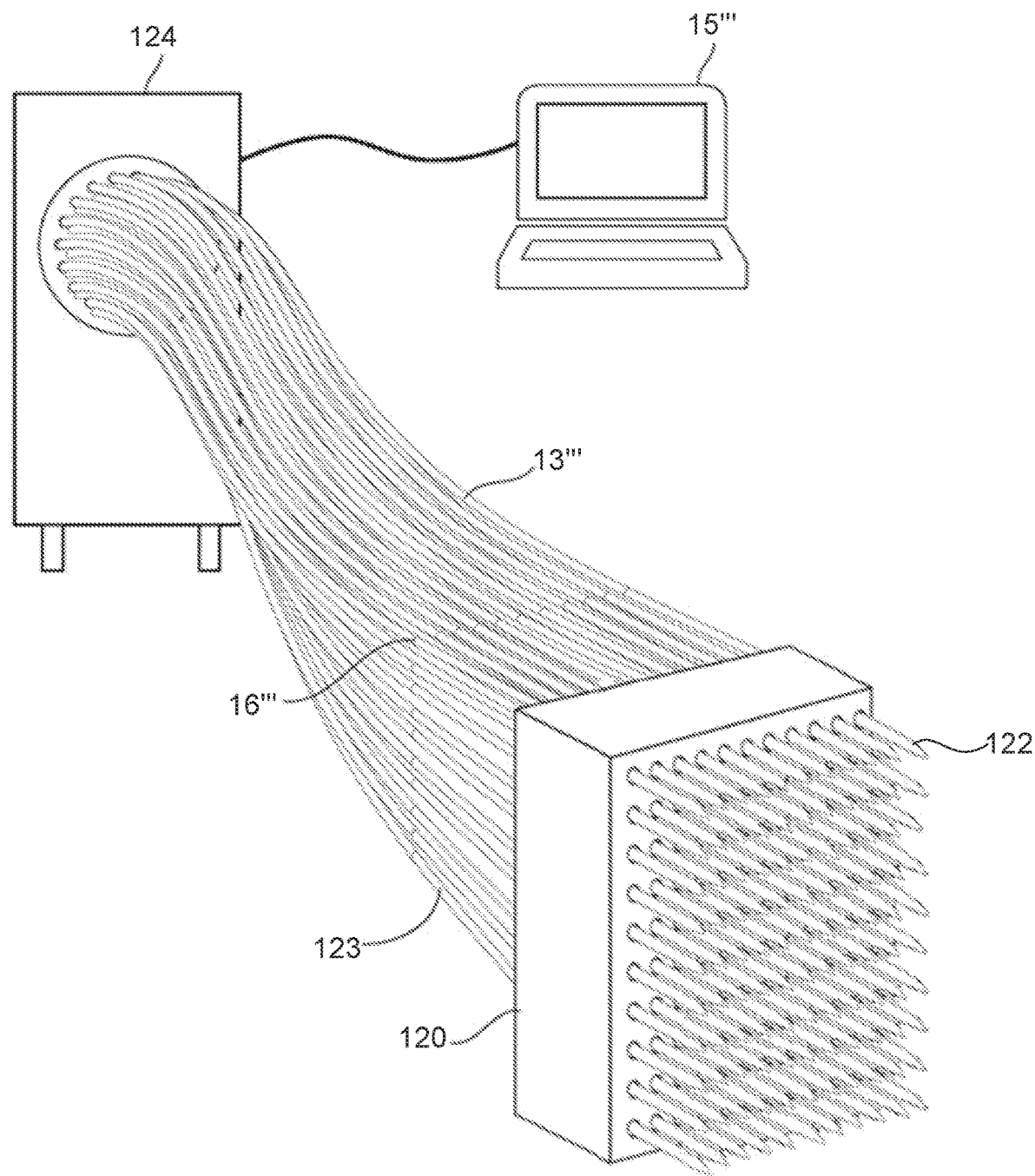
FIG. 15 illustrates the therapy system including the ultrasound transducer, applicator guide, and computing device for delivering ultrasound energy.

As shown in FIG. 15, the distal end of transfer tubes 123 may include piezoelectric element 122, operatively coupled to power generator 124. Transfer tubes 123 may be coupled to power generator 124 via transfer tubes 13''' and connecting interface 16'''. Computing device 15''' may be a standalone computing device, or may be incorporated into power generator 124. Power generator 124 may be programmed to cause piezoelectric element 122 to vibrate and emit ultrasound energy to the target area on/within the patient's skin sufficient to ablate the target tissue. For example, piezoelectric element 122 may be guided by applicator guide 120 to conform to the contours of the patient's skin at the target area, such that ultrasound energy may be uniformly delivered to the target tissue. In some embodiments, piezoelectric element 122 may be locked into place relative to applicator guide 120, and may non-invasively penetrate a stratum corneum (SC) of the patient's skin to deliver ultrasound energy within the patient's skin at the target area.

Alternatively, power generator 124 may be programmed to deliver ultrasound energy to the target area on/within the patient's skin sufficient for ultrasound imaging, such that one or more piezoelectric element 122 functions as an ultrasound imaging probe. Computing device 15''' may communicate with power generator 124 via any well-known wired or wireless connection (BlueTooth, Wi-Fi Direct, etc.). The clinician may adjust ultrasound energy emission and treatment time using computing device 15''' to control power generator 124 to deliver the appropriate amount of the ultrasound energy to a patient, e.g., for ablation and/or imaging.

Figure 16:
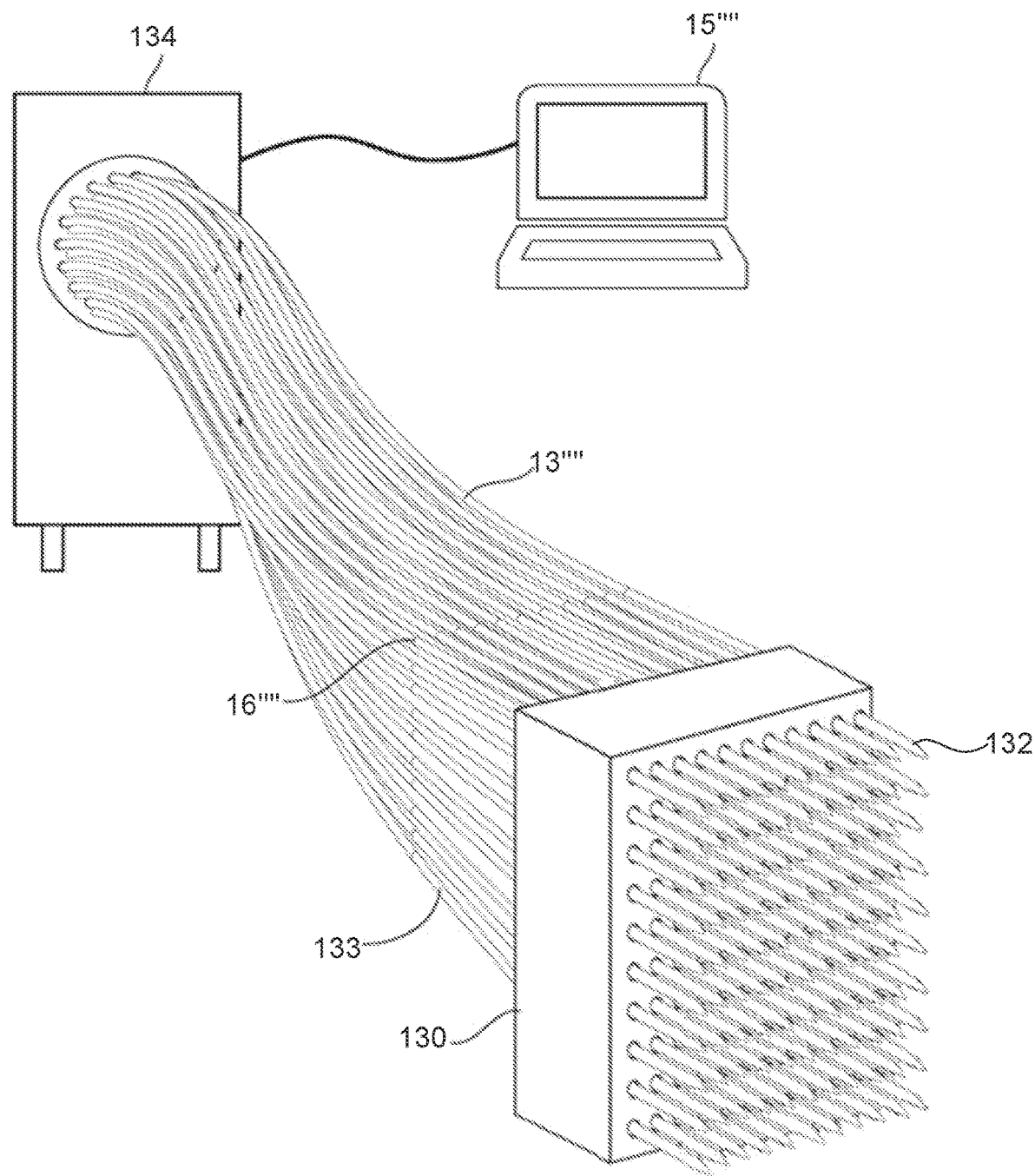
FIG. 16 illustrates the therapy system including the laser energy source, applicator guide, and computing device for delivering laser energy.

As shown in FIG. 16, the distal end of transfer tubes 133 may have laser emitter 132, operatively coupled to energy source 134. Transfer tubes 133 may be coupled to energy source 134 via transfer tubes 13'''' and connecting interface 16''''. Computing device 15'''' may be a standalone computing device, or may be incorporated into energy source 134. Energy source 134 may be programmed to cause laser emitter 132 to emit laser energy to the target area on/within the patient's skin sufficient to ablate the target tissue. For example, laser emitter 132 may be guided by applicator guide 130 to conform to the contours of the patient's skin at the target area, such that laser energy may be uniformly delivered to the target tissue.

Alternatively, energy source 134 may be programmed to deliver laser energy to the target area within the patient's skin (e.g., sufficient for depigmentation such as tattoo removal). Accordingly, laser emitter 132 may be locked into place relative to applicator guide 130, and may non-inva-

What is claimed is:

1. A therapy delivery system, the system comprising:
an applicator guide having a plurality of through hole channels extending from a first side of the applicator guide to a second side of the applicator guide, the plurality of through hole channels arranged in an array; and
a plurality of catheters configured to deliver a therapy, each catheter of the plurality of catheters disposed in respective through hole channels of the plurality of through hole channels in the applicator guide, the plurality of catheters independently and freely movable in at least one degree of freedom within the respective through hole channels such that the plurality of catheters are configured to conform to contours of an area of the patient's skin and to contact the area in a conformed orientation,
wherein the plurality of catheters are configured to deliver therapy to at least a portion of the area of the patent's skin while the plurality of catheters are positioned in the conformed orientation.

2. The system of claim 1, wherein the plurality of catheters comprise a plurality of microneedles configured to non-invasively penetrate a stratum corneum (SC) of the patient's skin, such that the plurality of microneedles are configured to selectively deliver therapy to the at least a portion of the area transdermally.

3. The system of claim 2, wherein the applicator guide comprises a plurality of locks, each one of the plurality of locks operatively coupled to a respective one of the plurality of microneedles to lock the respective one of the plurality of microneedles in the conformed orientation, such that the plurality of microneedles are configured to non-invasively penetrate the stratum corneum (SC) of the patient's skin in the conformed orientation.

4. The system of claim 3, wherein the plurality of locks are configured to be activated individually or together.

5. The system of claim 2, wherein the plurality of microneedles are configured to selectively deliver a drug to the at least a portion of the area transdermally.

6. The system of claim 5, wherein the plurality of microneedles are coated with the drug.

7. The system of claim 5, wherein the plurality of microneedles comprise an internal lumen, such that the drug is configured to be delivered to the at least a portion of the area transdermally through the internal lumen of the plurality of microneedles.

8. The system of claim 5, wherein the drug is embedded within the plurality of microneedles, and wherein at least a portion of the plurality of microneedles is configured to dissolve to deliver the drug to the at least a portion of the area transdermally.

9. The system of claim 1, wherein the plurality of catheters are operatively coupled to a pulse generator, and configured to selectively deliver RF energy to the at least a portion of the area.

10. The system of claim 1, wherein the plurality of catheters are operatively coupled to an ultrasound transducer, and configured to selectively deliver ultrasound energy to the at least a portion of the area.

11. The system of claim 1, wherein the plurality of catheters are operatively coupled to an afterloader, and configured to selectively deliver radiotherapy to the at least a portion of the area.

12. The system of claim 11, wherein each of the plurality of catheters is configured to be individually activated to deliver radiation.

13. The system of claim 11, wherein the afterloader is connected to each one of the plurality of catheters via a plurality of transfer tubes, the system further comprising a computing device in communication with the afterloader and configured to instruct the afterloader to deliver radioactive material to the plurality of catheters.

14. The system of claim 1, wherein one or more of the plurality of catheters is configured to apply heat while simultaneously delivering therapy to the at least a portion of the area.

15. A method for delivering therapy to a patient, the method comprising:
positioning an applicator guide over a target area of the patient, the applicator guide comprising a plurality of through hole channels;
loading a plurality of catheters into through hole channels of the plurality of through hole channels such that each of the plurality of through hole channels is loaded with a catheter of the plurality of catheters;
conforming the plurality of catheters to the target area of the patient, the plurality of catheters independently and freely movable within the through hole channels in at least one degree of freedom such that the plurality of catheters are configured to conform to contours of the target area of the patient in a conformed orientation; and
delivering therapy to the target area of the patient via at least one of the plurality of catheters in the conformed orientation.

16. The method of claim 15, wherein the plurality of catheters comprises a plurality of microneedles, and wherein the method further comprises locking the microneedles in the conformed orientation.

17. The method of claim 16, further comprising penetrating a stratum corneum (SC) of the patient's skin with the plurality of microneedles in the conformed orientation, and wherein delivering therapy to the target area of the patient comprises delivering therapy to the target area of the patient transdermally.

18. The method of claim 17, wherein delivering therapy to the target area of the patient transdermally comprises delivering a drug to the target area of the patient.

19. The method of claim 17, wherein delivering therapy to the target area of the patient transdermally comprises delivering energy to the target area of the patient.

20. The method of claim 15, wherein delivering therapy to the target area of the patient comprises delivering radioactive material to at least one of the plurality of catheters.

* * * * *